(12) United States Patent
Igarashi et al.

(10) Patent No.: US 11,436,729 B2
(45) Date of Patent: Sep. 6, 2022

(54) MEDICAL IMAGE PROCESSING APPARATUS

(71) Applicant: CANON MEDICAL SYSTEMS CORPORATION, Otawara (JP)

(72) Inventors: Yu Igarashi, Utsunomiya (JP); Masaki Watanabe, Utsunomiya (JP); Yasunori Honjo, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 120 days.

(21) Appl. No.: 16/809,628

(22) Filed: Mar. 5, 2020

(65) Prior Publication Data

US 2020/0334818 A1 Oct. 22, 2020

(30) Foreign Application Priority Data

Mar. 6, 2019 (JP) .............................. JP2019-040210
Mar. 6, 2019 (JP) .............................. JP2019-040211

(51) Int. Cl.

| G06K 9/00 | (2022.01) |
|---|---|
| G06T 7/00 | (2017.01) |
| G06K 9/62 | (2022.01) |
| A61B 8/08 | (2006.01) |
| A61B 5/055 | (2006.01) |
| A61B 6/03 | (2006.01) |

(52) U.S. Cl.
CPC .......... *G06T 7/0016* (2013.01); *G06K 9/6267* (2013.01); *A61B 5/055* (2013.01); *A61B 6/032* (2013.01); *A61B 8/481* (2013.01); *G06T 2207/10132* (2013.01); *G06T 2207/30056* (2013.01); *G06T 2207/30096* (2013.01)

(58) Field of Classification Search
CPC ......... G06T 7/0016; G06T 2207/10132; G06T 2207/30056; G06T 2207/30096; G06K 9/6267; A61B 5/055; A61B 6/032; A61B 8/481

See application file for complete search history.

(56) References Cited

U.S. PATENT DOCUMENTS

| 2009/0131796 | A1 | 5/2009 | Shen |
|---|---|---|---|
| 2010/0198054 | A1* | 8/2010 | Ewing .................... A61B 5/055 600/420 |
| 2011/0245675 | A1 | 10/2011 | Yoshida et al. |
| 2011/0282194 | A1 | 11/2011 | Reiner |
| 2017/0252011 | A1 | 9/2017 | Abe |
| 2018/0008235 | A1 | 1/2018 | Hayashi et al. |
| 2018/0025112 | A1 | 1/2018 | Takeda |
| 2019/0090832 | A1* | 3/2019 | Bao ........................ A61B 6/484 |
| 2019/0336107 | A1* | 11/2019 | Hope Simpson ... G01S 15/8979 |

* cited by examiner

*Primary Examiner* — Atiba O Fitzpatrick
(74) *Attorney, Agent, or Firm* — Oblon, McClelland, Maier & Neustadt, L.L.P.

(57) ABSTRACT

The medical image processing apparatus according to the present embodiment includes processing circuitry. The processing circuitry is configured to acquire contrast image data generated by imaging a subject. The processing circuitry is configured to input the acquired contrast image data to a learned model to generate a time phase data classified according to a contrast state of a lesion area with a contrast agent included in the acquired contrast image data, the learned model being for generating the time phase data based on the acquired contrast image data.

8 Claims, 18 Drawing Sheets

| CONTRAST IMAGE DATA S | NEEDFULNESS DATA T |
|---|---|
| CONTRAST IMAGE DATA IN EARLY VASCULAR PHASE | NECESSITY "1" |
| CONTRAST IMAGE DATA IN EARLY VASCULAR PHASE | UNNECESSITY "0" |
| CONTRAST IMAGE DATA IN EARLY VASCULAR PHASE | UNNECESSITY "0" |
| CONTRAST IMAGE DATA IN ARTERIAL PREDOMINANT PHASE | NECESSITY "1" |
| CONTRAST IMAGE DATA IN PORTAL PREDOMINANT PHASE | UNNECESSITY "0" |
| ⋮ | ⋮ |

MEDICAL IMAGE PROCESSING APPARATUS

CROSS-REFERENCE TO RELATED APPLICATION

This application is based upon and claims the benefit of priority from Japanese Patent Application No. 2019-040210, filed on Mar. 6, 2019, and Japanese Patent Application No. 2019-040211, filed on Mar. 6, 2019, the entire contents of each of which are incorporated herein by reference.

FIELD

An embodiment as an aspect of the present invention relates to a medical image processing apparatus.

BACKGROUND

In the medical field, an ultrasonic diagnostic apparatus is used for imaging the inside of a subject using ultrasonic waves generated by multiple transducers (piezoelectric vibrators) of an ultrasonic probe. The ultrasonic diagnostic apparatus causes the ultrasonic probe, which is connected to the ultrasonic diagnostic apparatus, to transmit ultrasonic waves into the subject, generates a reception signal based on a reflected wave, and acquires a desired ultrasonic image by image processing.

In a contrast examination using the ultrasonic diagnostic apparatus, after injection of a contrast agent, it is classified into multiple time phases according to the degree of contrast of a tumor with the contrast agent. For example, when the liver is imaged, it is classified into a time phase such as an early vascular phase, an arterial predominant phase, a portal predominant phase, or a post vascular phase based on an elapsed time from the start of the injection of the contrast agent. The time phase means a classification based on a contrast state of a lesion area with a contrast agent included in contrast image data. A definite diagnosis of the tumor is performed in real time based on the contrast image data acquired in any of these time phases, or the multiple contrast image data acquired in the respective multiple different time phases.

DETAILED DESCRIPTION

Figure 1:
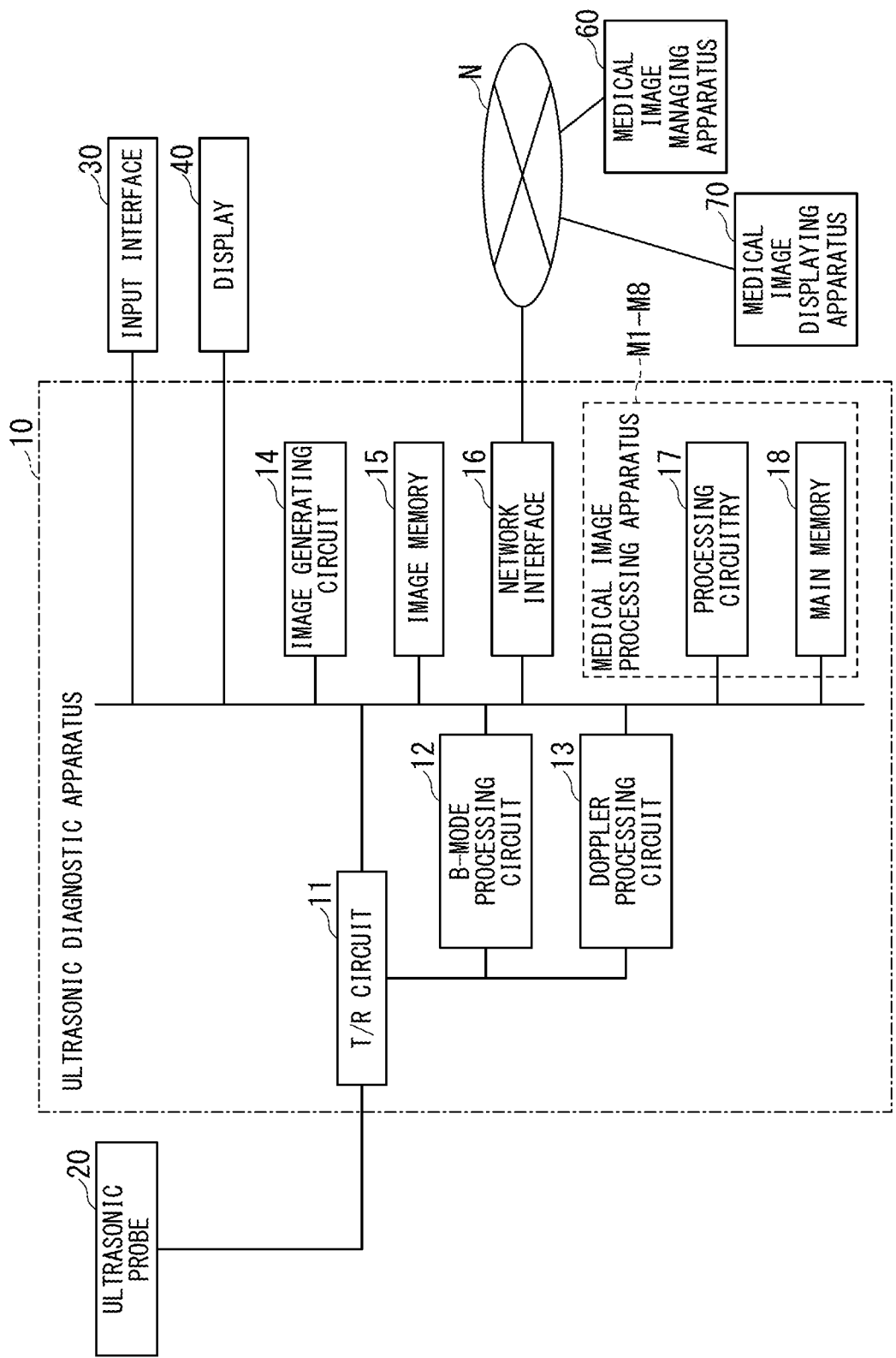
FIG. 1 is a schematic diagram showing a configuration of an ultrasonic diagnostic apparatus including a medical image processing apparatus according to an embodiment.

A medical image processing apparatus according to a present embodiment will be described with reference to the accompanying drawings.

The medical image processing apparatus according to the present embodiment includes processing circuitry. The processing circuitry is configured to acquire contrast image data generated by imaging a subject. The processing circuitry is configured to input the acquired contrast image data to a learned model to generate a time phase data classified according to a contrast state of a lesion area with a contrast agent included in the acquired contrast image data, the learned model being for generating the time phase data based on the acquired contrast image data.

The medical image processing apparatus according to the embodiment is provided in a medical image generating apparatus (also referred to as "modality") capable of acquiring contrast image data, for example, an ultrasonic diagnostic apparatus, an X-ray computed tomography (CT) apparatus, a magnetic resonance imaging (MRI) apparatus, or the like. The medical image processing apparatus according to the embodiment is provided in a medical image displaying apparatus capable of acquiring contrast image data from the medical image generating apparatus (or a medical image managing apparatus) via a network, for example, a workstation. Alternatively, the medical image processing apparatus according to the embodiment is provided in an off-line medical image displaying apparatus capable of acquiring contrast image data from the medical image generating apparatus (or the medical image managing apparatus) via a portable recording medium.

When the medical image processing apparatus is provided in the ultrasonic diagnostic apparatus as the medical image generating apparatus, it is possible to classify a time phase after injection of a contrast agent into any of multiple time phases (e.g., an early vascular phase, an arterial predominant phase, a portal predominant phase, and a post vascular phase) with a contrast scan of the liver. When the medical image processing apparatus is provided in the X-ray CT apparatus as the medical image generating apparatus, it is possible to classify a time phase a after injection of a contrast agent into any of multiple time phases (e.g., an arterial predominant phase, a portal predominant phase, and an equilibrium phase) with a contrast scan of the liver. Further, when the medical image processing apparatus is provided in the MRI apparatus as the medical image generating apparatus, it is possible to classify a time phase after injection of a contrast agent into any of multiple time phases (e.g., a dynamic phase and a hepatocyte contrast phase) with a contrast scan of the liver.

Hereinafter, in each of the first to eighth embodiments, a case where the medical image processing apparatus is provided in the ultrasonic diagnostic apparatus will be described as an example. In the ninth embodiment, a case where the medical image processing apparatus is provided in the medical image displaying apparatus will be described as an example.

Hereinafter, a case where the imaging region is the liver will be described. However, it is not limited to that case. The imaging region may be a tissue that can specify a specific contrast state of a lesion area with a contrast agent, for example, the mammary gland or the pancreas.

1. Medical Image Processing Apparatus According to the First Embodiment

FIG. 1 is a schematic diagram showing a configuration of an ultrasonic diagnostic apparatus including a medical image processing apparatus according to the first embodiment.

FIG. 1 shows an ultrasonic diagnostic apparatus 10 including a medical image processing apparatus according to the first embodiment. FIG. 1 shows an ultrasonic probe 20, an input interface 30, and a display 40. Note that an apparatus in which at least one of the ultrasonic probe 20, the input interface 30 and the display 40 are added to the ultrasonic diagnostic apparatus 10 may be referred to as "ultrasonic diagnostic apparatus". In the following description, a case will be described in which the ultrasonic probe 20, the input interface 30 and the display 40 are all provided outside "ultrasonic diagnostic apparatus".

The ultrasonic diagnostic apparatus 10 includes a transmitting/receiving (T/R) circuit 11, a B-mode processing circuit 12, a Doppler processing circuit 13, an image generating circuit 14, an image memory 15, a network interface 16, processing circuitry 17, and a main memory 18. The circuits 11 to 14 are configured by application-specific integrated circuits (ASICs) and the like. However, the present invention is not limited to this case, and all or part of the functions of the circuits 11 to 14 may be realized by the processing circuitry 17 executing a program. Further, the processing circuitry 17 and the main memory 18 constitute a medical image processing apparatus M1 according to the first embodiment. The medical image processing apparatus M1 according to the first embodiment may be configured by adding at least one of the input interface 30 and the display 40 to the processing circuitry 17 and the main memory 18.

The T/R circuit 11 has a transmitting circuit and a receiving circuit (not shown). Under the control of the processing circuitry 17, the T/R circuit 11 controls transmission directivity and reception directivity in transmission and reception of ultrasonic waves. The case where the T/R circuit 11 is provided in the ultrasonic diagnostic apparatus 10 will be described, but the T/R circuit 11 may be provided in the ultrasonic probe 20, or may be provided in both of the ultrasonic diagnostic apparatus 10 and the ultrasonic probe 20. The T/R circuit 11 is one example of a transmitter-and-receiver.

The transmitting circuit has a pulse generating circuit, a transmission delay circuit, a pulsar circuit, and the like, and supplies a drive signal to ultrasonic transducers. The pulse generating circuit repeatedly generates rate pulses for forming transmission ultrasonic waves at a predetermined rate frequency. The transmission delay circuit converges the ultrasonic waves generated from the ultrasonic transducer of the ultrasonic probe 20 into a beam shape, and gives a delay time of each piezoelectric transducer necessary for determining the transmission directivity to each rate pulse generated by the pulse generating circuit. In addition, the pulsar circuit applies drive pulses to each ultrasonic transducer at a timing based on the rate pulses. The transmission delay circuit arbitrarily adjusts the transmission direction of the ultrasonic beam transmitted from a piezoelectric transducer surface by changing the delay time given to each rate pulse.

The receiving circuit includes an amplifier circuit, an analog to digital (A/D) converter, an adder, and the like. The receiving circuit receives echo signals received by the ultrasonic transducers and performs various processes on the echo signals to generate echo data. The amplifier circuit amplifies the echo signals for each channel and performs the gain correction processing. The A/D converter performs A/D conversion of the gain-corrected echo signals, and gives a delay time necessary for determining reception directivity to digital data. The adder performs the addition processing on the echo signals processed by the A/D converter to generate echo data. With the addition processing of the adder, the reflection component from the direction corresponding to each reception directivity of the echo signals is emphasized.

Under the control of the processing circuitry 17, the B-mode processing circuit 12 receives the echo data from the receiving circuit, performs logarithmic amplification, envelope detection processing and the like, thereby generate data (2D or 3D data) which signal intensity is represented by brightness of luminance. This data is generally called "B-mode data". The B-mode processing circuit 12 is one example of a B-mode processor.

The B-mode processing circuit 12 may change the frequency band to be visualized by changing the detection frequency using filtering processing. By using the filtering processing function of the B-mode processing circuit 12, harmonic imaging such as the contrast harmonic imaging (CHI) or the tissue harmonic imaging (THI) is performed. That is, the B-mode processing circuit 12 may separate the reflected wave data into harmonic data (or sub-frequency data) and fundamental wave data within a subject into which the contrast agent is injected. The harmonic data (or sub-frequency data) corresponds to reflected wave data with a harmonic component whose reflection source is the contrast agent (microbubbles or bubbles) in the subject. The fundamental wave data corresponds to reflected wave data with a fundamental wave component whose reflection source is tissue in the subject. The B-mode processing circuit 12 generates B-mode data for generating contrast image data based on the reflected wave data (reception signals) with the harmonic component, and generates B-mode data for generating fundamental wave image data based on the reflected wave data (reception signals) with the fundamental wave component.

Under the control of the processing circuitry 17, the Doppler processing circuit 13 frequency-analyzes the phase information from the echo data from the receiving circuit, thereby generating data (two-dimensional (2D) or three-dimensional (3D) data) acquired by extracting dynamic data of moving subject such as average speed, dispersion, power and the like for multiple points. This data is generally called "Doppler data". In the present embodiment, the moving subject is, for example, blood flow, tissue such as heart wall, or contrast agent. The Doppler processing circuit 13 is one example of a Doppler processor.

Under the control of the processing circuitry 17, the image generating circuit 14 generates ultrasonic image data presented in a predetermined luminance range based on the reception signals received by the ultrasonic probe 20. For example, the image generating circuit 14 generates, as the ultrasonic image data, 2D B-mode image data in which the intensity of the reflected wave is represented by luminance based on 2D B-mode data generated by the B-mode processing circuit 12. In addition, the image generating circuit 14 generates, as the ultrasonic image data, 2D color Doppler image data based on 2D Doppler data generated by the Doppler processing circuit 13. The 2D color Doppler image includes an average speed image representing moving state information, a dispersion image, a power image, or a combination image thereof. Hereinafter, 2D ultrasonic image data such as the 2D B-mode image data and the 2D color Doppler image data will be simply referred to as "2D image data".

In the present embodiment, the image generating circuit 14 generally converts (scan-converts) a scanning line signal sequence of ultrasonic scanning into a scanning line signal sequence of a video format used by a television or the like, and generates image data for display. Specifically, the image generating circuit 14 generates image data for display by performing coordinate conversion according to the ultrasonic scanning mode of the ultrasonic probe 20. The image generating circuit 14 performs various image processes other than the scan conversion. For example, the image generating circuit 14 performs image processing (smoothing processing) for regenerating an average luminance image using multiple image frames after scan conversion, image processing using a differential filter in the image (processing for enhancing edges) and the like. Further, the image generating circuit 14 combines character information of various parameters, scales, body marks, and the like with the ultrasonic image data.

That is, the B-mode data and the Doppler data are the image data before the scan conversion processing. The data generated by the image generating circuit 14 is the image data for display after the scan conversion processing. The B-mode data and the Doppler data are also called raw data. The image generating circuit 14 generates 2D image data for display from the 2D image data before the scan conversion processing.

Further, the image generating circuit 14 performs coordinate conversion on the 3D B-mode data generated by the B-mode processing circuit 12, thereby generates 3D B-mode image data. The image generating circuit 14 performs coordinate conversion on the 3D Doppler data generated by the Doppler processing circuit 13, thereby generates 3D Doppler image data. The image generating circuit 14 generates the 3D B-mode image data or the 3D Doppler image data as 3D image data (volume data).

Further, the image generating circuit 14 performs the rendering processing on the 3D image data to generate various 2D image data for displaying the 3D image data on the display 40. The image generating circuit 14 performs the volume rendering (VR) processing for generating 2D image data reflecting 3D information, for example, as rendering processing. Further, the image generating circuit 14 performs the processing for generating multi-planer reconstruction (MPR) image data from the 3D image data by performing an MPR method. The image generating circuit 14 is one example of an image generator.

The image memory 15 includes multiple memory cells in one frame in two axial directions, and includes a two-dimensional memory which is a memory provided with multiple frames. The two-dimensional memory as the image memory 15 stores one frame or multiple frames of the 2D image data generated by the image generating circuit 14 under the control of the processing circuitry 17. The image memory 15 is one example of a storage.

Under the control of the processing circuitry 17, the image generating circuit 14, if necessary, performs 3D reconstruction for performing an interpolation processing on the multiple 2D image data arranged in the 2D memory as the image memory 15, thereby generates the multiple 2D image data as the 3D image data in the 3D memory as the image memory 15. A known technique is used as the interpolation processing.

The image memory 15 may include a 3D memory which is a memory having multiple memory cells in three axis directions (X-axis, Y-axis, and Z-axis directions). The 3D memory as the image memory 15 stores the multiple 2D image data generated by the image generating circuit 14 as the 3D image data under the control of the processing circuitry 17.

The network interface 16 implements various information communication protocols according to the network form. The network interface 16 connects the ultrasonic diagnostic apparatus 10 and other devices such as the external medical image managing apparatus 60 and the medical image displaying apparatus 70 according to these various protocols. An electrical connection or the like via an electronic network is applied to this connection. In the present embodiment, the electronic network means an entire information communication network using telecommunications technology. The electronic network includes a wired/wireless hospital backbone local area network (LAN) and the Internet network, as well as a telephone communication line network, an optical fiber communication network, a cable communication network, a satellite communication network, or the like.

Further, the network interface 16 may implement various protocols for non-contact wireless communication. In this case, the ultrasonic diagnostic apparatus 10 can directly transmit/receive data to/from the ultrasonic probe 20, for example, without going through the network. The network interface 16 is one example of a network connector.

The processing circuitry 17 may refer to a dedicated or general-purpose central processing unit (CPU), an microprocessor unit (MPU), a graphics processing unit (GPU), or the like. The processing circuitry 17 may refers to an ASIC, a programmable logic device, or the like. The programmable logic device is, for example, a simple programmable logic device (SPLD), a complex programmable logic device (CPLD), and a field programmable gate array (FPGA).

Further, the processing circuitry 17 may be constituted by a single circuit or a combination of independent circuit elements. In the latter case, the main memory 18 may be provided individually for each circuit element, or a single main memory 18 may store programs corresponding to the functions of the circuit elements.

The main memory 18 is constituted by a semiconductor memory element such as a random-access memory (RAM), a flash memory, a hard disk, an optical disk, or the like. The main memory 18 may be constituted by a portable medium such as a universal serial bus (USE) memory and a digital video disk (DVD). The main memory 18 stores various processing programs (including an operating system (CS) and the like besides the application program) used in the processing circuitry 17 and data necessary for executing the programs. In addition, the OS may include a graphical user interface (GUI) which allows the operator to frequently use graphics to display information on the display 40 to the operator and can perform basic operations by the input interface 30. The main memory 18 is one example of a storage.

The ultrasonic probe 20 includes microscopic transducers (piezoelectric elements) on the front surface portion, and transmits and receives ultrasonic waves to a region including an imaging region. Each transducer is an electroacoustic transducer, and has a function of converting electric pulses into ultrasonic pulses at the time of transmission and converting reflected waves to electric signals (reception signals) at the time of reception. The ultrasonic probe 20 is configured to be small and lightweight, and is connected to the ultrasonic diagnostic apparatus 10 via a cable (or wireless communication).

The ultrasonic probe 20 is classified into types such as a linear type, a convex type, a sector type, etc. depending on differences in scanning system. Further, the ultrasonic probe 20 is classified into a 1D array probe in which transducers are arrayed in a one-dimensional (1D) manner in the azimuth direction, and a 2D array probe in which transducers are arrayed in a 2D manner in the azimuth direction and in the elevation direction, depending on the array arrangement dimension. The 1D array probe includes a probe in which a small number of transducers are arranged in the elevation direction.

In the present embodiment, when an imaging, that is, a panoramic scan is executed, the 2D array probe having a scan type such as the linear type, the convex type, the sector type, or the like is used as the ultrasonic probe 20. Alternatively, when the imaging is executed, the 1D probe having a scan type such as the linear type, the convex type, the sector type and the like and having a mechanism that mechanically oscillates in the elevation direction is used as the ultrasonic probe 20. The latter probe is also called a mechanical 4D probe.

The input interface 30 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 30 generates an input signal corresponding to the operation and outputs it to the processing circuitry 17. The input interface 30 is one example of an input unit.

The display 40 is constituted by a general display output device such as a liquid crystal display or an organic light emitting diode (OLED) display. The display 40 displays various kinds of information under the control of the processing circuitry 17. The display 40 is one example of a display unit.

Further, FIG. 1 shows the medical image managing apparatus 60 and the medical image displaying apparatus 70 which are external devices of the ultrasonic diagnostic apparatus 10. The medical image managing apparatus 60 is, for example, a digital imaging and communications in medicine (DICOM) server, and is connected to a device such as the ultrasonic diagnostic apparatus 10 such that data can be transmitted and received via the network N. The medical image managing apparatus 60 manages a medical image such as an ultrasonic image generated by the ultrasonic diagnostic apparatus 10 as a DICOM file.

The medical image displaying apparatus 70 is connected to devices such as the ultrasonic diagnostic apparatus 10 and the medical image managing apparatus 60 such that data is transmitted and received via the network N. An Example of the medical image displaying apparatus 70 includes a workstation that performs various image processing on the ultrasonic image generated by the ultrasonic diagnostic apparatus 10 and a portable information processing terminal such as a tablet terminal. It should be noted that the medical image displaying apparatus 70 is an offline apparatus and may be an apparatus capable of reading an ultrasonic image generated by the ultrasonic diagnostic apparatus 10 via a portable storage medium.

Subsequently, functions of the ultrasonic diagnostic apparatus 10 including the medical image processing apparatus M1 will be described.

Figure 2:
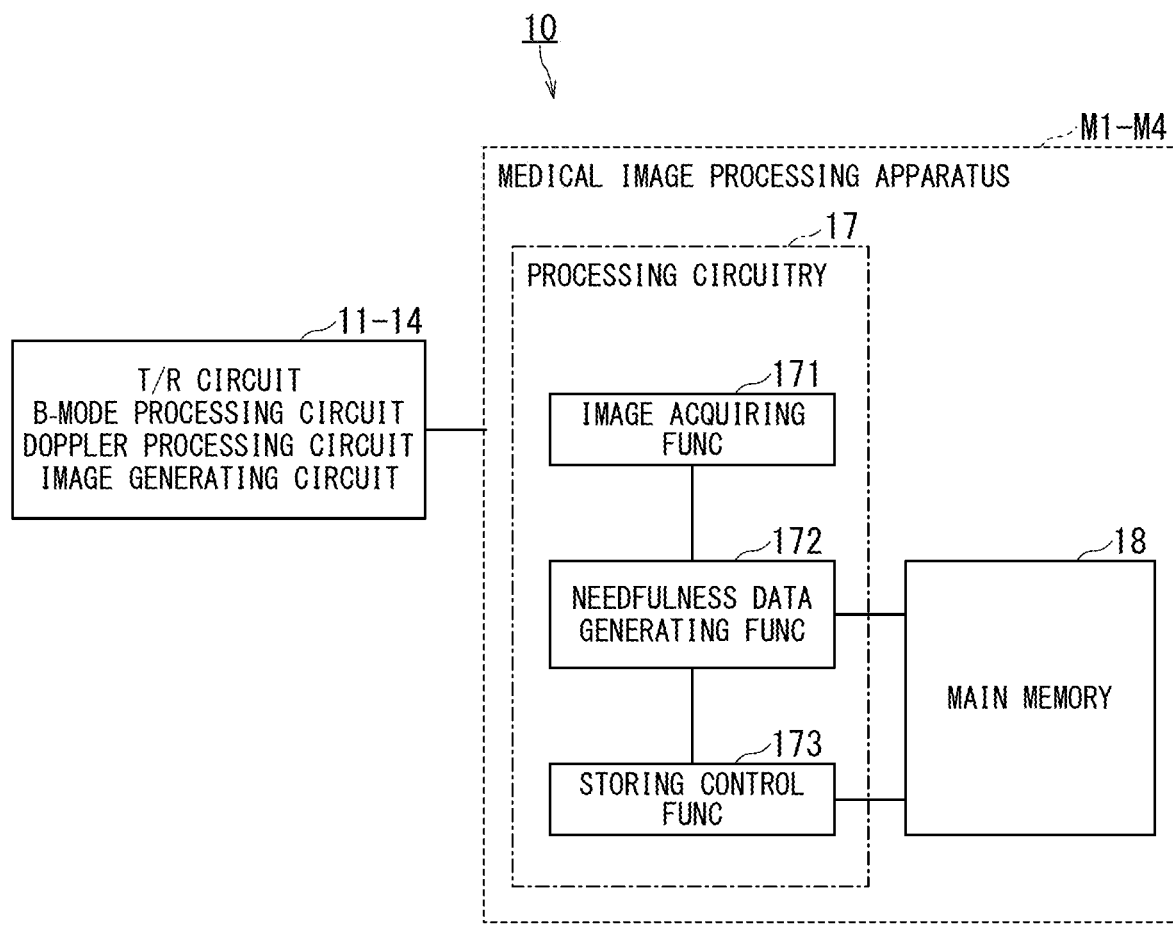
FIG. 2 is a block diagram showing functions of the ultrasonic diagnostic apparatus including the medical image processing apparatus according to the embodiment.

FIG. 2 is a block diagram showing functions of the ultrasonic diagnostic apparatus 10 including the medical image processing apparatus M1.

The processing circuitry 17 reads and executes a program stored in the main memory 18 or directly incorporated in the processing circuitry 17, thereby realizes an image acquiring function 171, a needfulness data generating function 172, and a storing control function 173. Hereinafter, a case where the functions 171 to 173 function as software will be described as an example. However, all or a part of the functions 171 to 173 may be provided in the ultrasonic diagnostic apparatus 10 as a circuit such as the ASIC.

The image acquiring function 171 includes a function of controlling the T/R circuit 11, the B-mode processing circuit 12, the Doppler processing circuit 13, the image generating circuit 14, and the like to execute ultrasonic imaging using the ultrasonic probe 20 and acquire multiple ultrasonic image data (e.g., contrast image data) in time series. The image acquiring function 171 is one example of an image acquiring unit.

In this embodiment, each contrast image data is able to be associated with information (Hereinafter, referred to as "time phase" or "time phase data") on a time phase classified by contrast state of a lesion area included in contrast image data by a contrast agent. This is because the time phase information is generally classified according to the elapsed time based on the start of injection of the contrast agent. Here, the time phase information means an early vascular phase, an arterial predominant phase, a portal predominant phase, a post vascular phase, or the like.

The needfulness data generating function 172 includes a function of inputting contrast image data of the subject into the learned model for generating data (needfulness data) regarding needfulness of storage on the basis of contrast image data necessary for the definite diagnosis of the tumor among the multiple contrast image data in each time phase, thereby generating the needfulness data for storing the contrast image data of the subject. The needfulness data generating function 172 is one example of a processing unit.

The storing control function 173 includes a function of controlling storage of the contrast image data of the subject in the main memory 18 according to the needfulness data generated by the needfulness data generating function 172. Further, it is preferable that the storing control function 173 has a function of storing the contrast image data in the main memory 18 in association with the dynamic image data from the contrast image data of multiple frames. The associated contrast image data is determined necessary to be stored among contrast image data of multiple frames of the subject generated by ultrasonic imaging. In this case, it is possible for an operator such as a doctor who refers to the dynamic image data on the ultrasonic diagnostic apparatus 10 or the medical image displaying apparatus 70 to easily take the contrast image data of the extracted frame as reference The storing control function 173 is one example of a storing control unit.

Details of the functions 171 to 173 will be described with reference to FIGS. 3 to 9.

Figure 3:
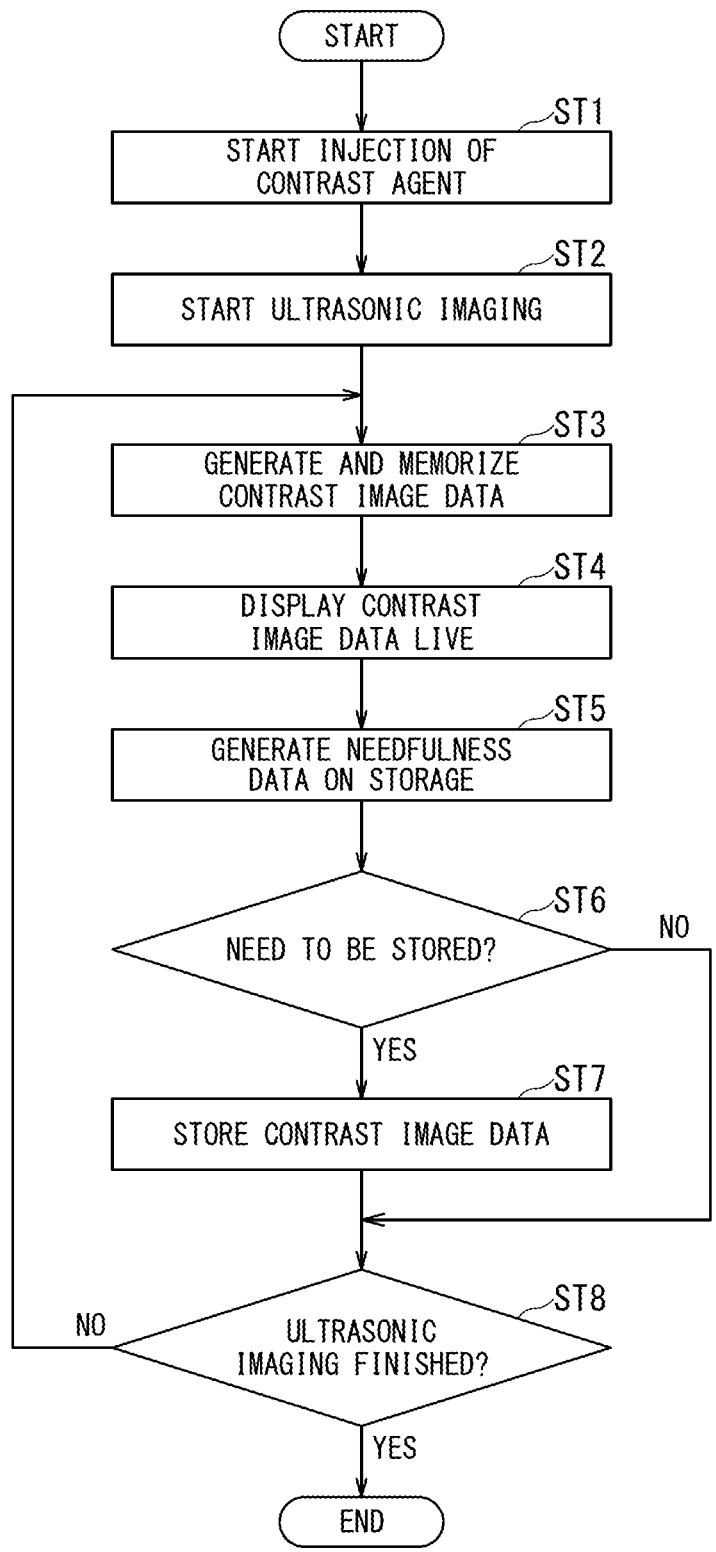
FIG. 3 is a flowchart showing an operation of the ultrasonic diagnostic apparatus including the medical image processing apparatus according to the embodiment.

FIG. 3 is a flowchart showing an operation of the ultrasonic diagnostic apparatus 10 including the medical image processing apparatus M1. In FIG. 3, reference numerals with numbers attached to "ST" indicate respective steps of the flowchart.

First, the image acquiring function 171 starts injection of a contrast agent (step ST1), and controls the T/R circuit 11, the B-mode processing circuit 12, the Doppler processing circuit 13, the image generating circuit 14, and the like, thereby starts ultrasonic imaging (e.g., CHI: Contrast Harmonic Imaging) using the ultrasonic probe 20 (step ST2). The image acquiring function 171 controls the image generating circuit 14 and the like to generate contrast image data and store it in the image memory 15 (step ST3). Further, the image acquiring function 171 displays the contrast image data generated in step ST3 live on the display 40 (step ST4).

The needfulness data generating function 172 generates needfulness data regarding a storage of the contrast image data on the basis of the contrast image data of the latest frame generated in step ST3 (step ST5). Here, it is also possible to associate the "time phase data" with each contrast image data.

In the embodiment, the needfulness data generating function 172 performs a processing of generating needfulness data regarding the storage of the contrast image data based on the contrast image data. For this processing, for example, a lookup table (LUT) that associates the contrast image data with the needfulness data regarding storage may be used. Machine learning may be used for this processing. Further, as the machine learning, deep learning using a multi-layer neural network such as convolutional neural network (CNN) or convolutional deep belief network (CDBN) may be used.

In the description of the first embodiment, an example is shown in which the needfulness data generating function 172 includes the neural network N1 and generates the needfulness data regarding the storage of the contrast image data on the basis of the contrast image data, using deep learning.

Figures 4A, 4B:
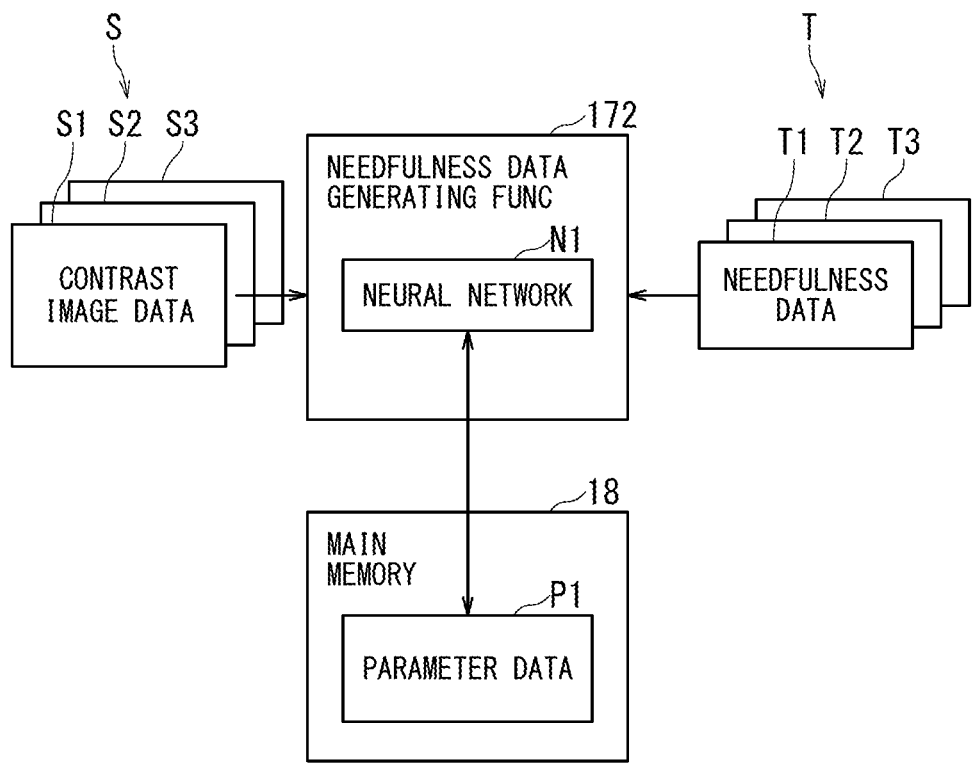
FIG. 4A is an explanatory diagram showing an example of a data flow during learning in the medical image processing apparatus according to the embodiment.
FIG. 4B is a diagram showing an example of training data as a table in the medical image processing apparatus according to the embodiment.

FIG. 4A is an explanatory diagram showing an example of a data flow during learning. FIG. 4B is a diagram showing an example of training data as a table. In FIG. 4B, each contrast image data is associated with the time phase data classified according to the contrast state in the lesion area with the contrast agent included in the contrast image data. When the needfulness data generating function 172 generates the needfulness data in substantially real time (or live) with respect to the multiple contrast image data sequentially acquired by the image acquiring function 171, the needfulness data generating function 172 can associate multiple time phase data with multiple contrast image data respectively. It should be noted that "substantially real time" includes the case where an ultrasonic image is generated (or displayed) at the same time as the ultrasonic wave is transmitted. Furthermore, "substantially real time" includes the case where there is a time lag from the transmission of ultrasonic waves to the generation (or display) of ultrasonic image. The time lag corresponds to the processing time from the transmission of ultrasonic waves to the generation (or display) of ultrasonic image.

The needfulness data generating function 172 sequentially updates parameter data P1 by receiving a large number of training data and performing learning. The training data is a combination of contrast image data S1, S2, S3, . . . as training input data and the needfulness data T1, T2, T3, . . . . The contrast image data S1 constitutes a training input data group S. The needfulness data T1, T2, T3, . . . constitutes a training output data group T.

The needfulness data generating function 172 updates the parameter data P1 each time the training data is input such that the result of processing the contrast image data S1, S2, S3, . . . by the neural network N1 approaches the needfulness data T1, T1, T3, . . . . . The needfulness data generating function 172 performs so-called learning. Generally, when the rate of change of the parameter data P1 converges within the threshold value, the learning is determined to be completed. Hereinafter, the parameter data P1 after learning is particularly referred to as learned parameter data P1' (shown in FIG. 5).

Figure 5:
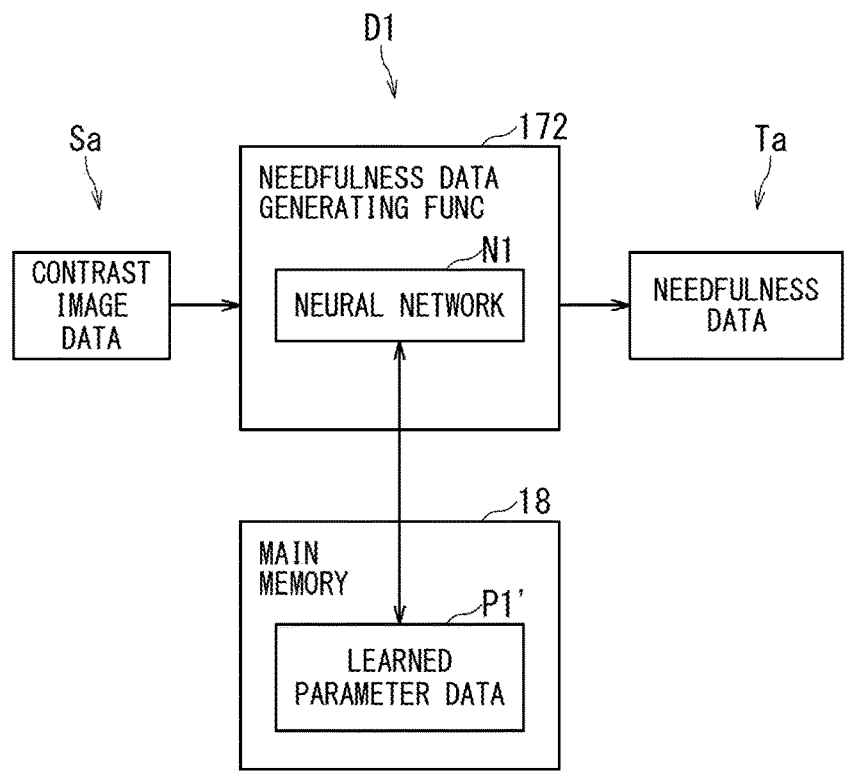
FIG. 5 is an explanatory diagram showing an example of a data flow during operation in the medical image processing apparatus according to the embodiment.

It should be noted that the type of training input data and the type of input data during operation shown in FIG. 5 should match. For example, when the input data during operation is the contrast image data of the subject, the training input data group S during learning is also the contrast image data.

Further, the "image data" includes raw data generated by a medical image generating apparatus such as an ultrasonic diagnostic apparatus. That is, the input data of the neural network N1 may be raw data before the scan conversion.

FIG. 5 is an explanatory diagram showing an example of a data flow during operation.

At the time of operation, the needfulness data generating function 172 inputs the contrast image data Sa of the subject to be diagnosed into the learned model D1, thereby outputs the needfulness data Ta regarding storage of the contrast image data of the subject using the learned parameter data P1'.

Further, the learned neural network N1 and the learned parameter P1' constitute the learned model D1. The neural network N1 is stored in the main memory 18 in the form of a program. The learned parameter data P1' may be stored in the main memory 18 or may be stored in a storage medium connected to the ultrasonic diagnostic apparatus 10 via the network N. In this case, the needfulness data generating function 172 realized by the processor of the processing circuitry 17 reads the learned model D1 from the main memory 18 and executes it, thereby generates the needfulness data regarding storage based on the contrast image data. The learned model D1 may be constructed by an integrated circuit such as an application specific integrated circuit (ASIC) and a field programmable gate array (FPGA).

It should be noted that the needfulness data Ta may be, for example, data indicating either necessity "1" or unnecessity "0". The needfulness data Ta is output by the learned model D1 including the needfulness data generating function 172, and relates to storage of contrast image data of the subject.

Further, as the input data, in addition to the contrast image data, identification information including at least one of the height, weight, medical history, and medical history of relatives of the imaging region may be used. This is to improve the accuracy of judgment by the needfulness data generating function 172.

In this case, at the time of learning, the identification information of each imaging target person of the contrast image data S1, S2, S3, . . . as the training input data is also input to the neural network N1 as the training input data. In operation, the needfulness data generating function 172 inputs the identification information of the subject with the contrast image data Sa of the subject to be diagnosed into the learned model D1 read from the main memory 18, thereby outputs the needfulness data Ta regarding storage of the contrast image data of the subject. By using the contrast image data and the identification information of the imaging target person as the input data, it is possible to generate the learned parameter data P1' that has been learned according to the type of the imaging target person. As a result, the diagnostic accuracy can be improved as compared with the case where only the contrast image data is used as the input data.

Returning to the description of FIG. 3, the storing control function 173 determines whether or not it is necessary to store the contrast image data generated in step ST3, according to the needfulness data regarding storage generated in step ST5 (step ST6). If it is determined as "YES" in step ST6, that is, if it is determined that the contrast image data generated in step ST3 needs to be stored, the storing control function 173 stores the contrast image data generated in step ST3 in the main memory 18 (step ST7). The storage in step ST7 is performed separately from the storage in step ST3. The storing control function 173 has a function of preferably associating the contrast image data determined necessary to be stored with the dynamic image data composed of the contrast image data of multiple frames, and then storing it in the main memory 18.

Figure 6:
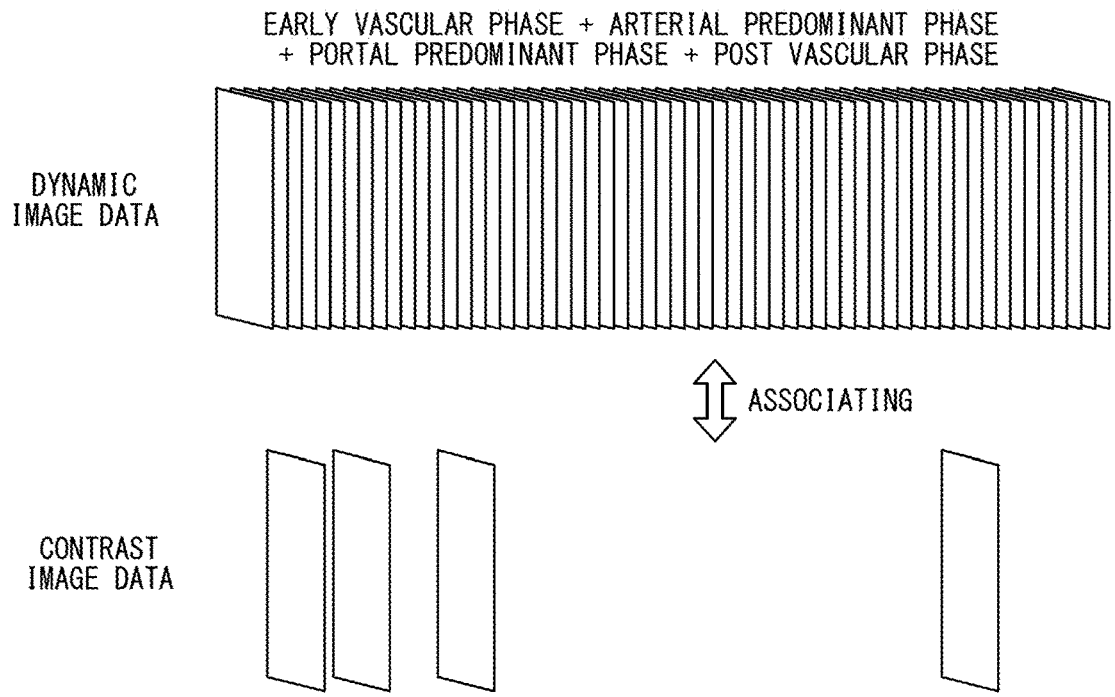
FIG. 6 is a diagram showing a concept of associating contrast image data with dynamic image data in the medical image processing apparatus according to the embodiment.

FIG. 6 is a diagram showing a concept of associating the contrast image data with the dynamic image data.

As shown in FIG. 6, the contrast image data of the subject determined to be necessary for storage is stored in the main memory 18 in association with the dynamic image data including the contrast image data of multiple frames. It is preferable that at least one contrast image data of each time phase is determined necessary to be stored.

Returning to the description of FIG. 3, after step ST7, if it is determined as "NO" in step ST6, that is, if it is determined unnecessary to store the contrast image data generated in step ST3, the image acquiring function 171 determines whether or not to finish the ultrasonic imaging started in step ST2 (step ST8).

If it is determined as "NO" in step ST8, that is, if it is determined that the ultrasonic imaging started in step ST2 is not to be terminated, the image acquiring function 171 controls the image generating circuit 14 and the like to generate contrast image data of a next frame and store it in the image memory 15 (step ST3). That is, the ultrasonic imaging is continued.

On the other hand, if it is determined as "YES" in step ST8, that is, if it is determined that the ultrasonic imaging started in step ST2 is to be finished, the image acquiring function 171 finishes the ultrasonic imaging. It is determined that the operator has given a finish instruction via the input interface 30.

That is, according to the flowchart shown in FIG. 3, the ultrasonic diagnostic apparatus 10 repeats the set of steps ST3 to ST8 to generate the needfulness data regarding storage for each frame, and stores it according to the needfulness data.

The contrast image data is not limited to the case of one frame image data. The contrast image data may be dynamic image data including multiple consecutive frames. In this case, the dynamic image data including the multiple contrast image data up to now is used as training input data, and dynamic image data of the subject to be diagnosed is used as input of the learned model D1 as contrast image data Sa. As a result, it is possible to learn dynamic moving of bubbles included in the contrast agent.

Further, according to the flowchart shown in FIG. 3, the needfulness data generating function 172 generates the needfulness data every time the contrast image data of each continuous frame is generated. However, it is not limited to this case. For example, the needfulness data generating function 172 may generate the needfulness every time the contrast image data of each frame generated at a constant frame interval is generated, or may generate the needfulness data each time the first frame of contrast image data for each phase is generated.

According to the medical image processing apparatus M1, by storing the contrast image data that is estimated necessary for separate diagnosis from the dynamic image data of the entire frame, the post processing with the stored image enables the definite diagnosis of the tumor without depending on the experience or subjectivity of an operator such as a doctor, and shortens the diagnosis time.

2. Medical Image Processing Apparatus According to the Second Embodiment

In the above-described first embodiment, the case where one neural network is configured regardless of the time phase has been described. That is, this is the case where the needfulness data generating function 172 inputs the contrast image data of the subject in each time phase to one learned model, thereby generates the needfulness data regarding the storage of the contrast image data of the subject in each time phase. However, it is not limited to this case.

For example, one neural network may be configured for each time phase. That is, the needfulness data generating function 172 inputs the contrast image data of the subject to the learned model corresponding to the time phase among multiple learned models corresponding to the time phases, and generates needfulness data regarding storage of contrast image data of the subject. This case will be described as a medical image processing apparatus M2 (shown in FIGS. 1 and 2) according to the second embodiment.

The configuration and function of the medical image processing apparatus M2 are the same as those shown in FIGS. 1 and 2. The operation of the medical image processing apparatus M2 is equivalent to that shown in FIG. 3. Therefore, their description is omitted.

In step ST5 shown in FIG. 3, the needfulness data generating function 172 shown in FIG. 2 generates the needfulness data regarding the storage of the contrast image data based on the contrast image data of the latest frame generated in step ST3.

In the embodiment, the needfulness data generating function 172 performs a processing of needfulness data regarding storage according to the time phase corresponding to the target frame. For this processing, for example, a lookup table for each time phase in which the contrast image data and the needfulness data regarding storage are associated may be used. Machine learning may be used for this processing. Further, deep learning using the multilayer neural network such as CNN or a convolutional deep belief network may be used as the machine learning.

In the description of the second embodiment, the case where the needfulness data generating function 172 includes multiple neural networks N2 (e.g., "N21" and "N22" shown in FIGS. 7A and 7B respectively), and where the needfulness data regarding storage is generated based on the contrast image data using deep learning is mentioned.

Figure 7A:
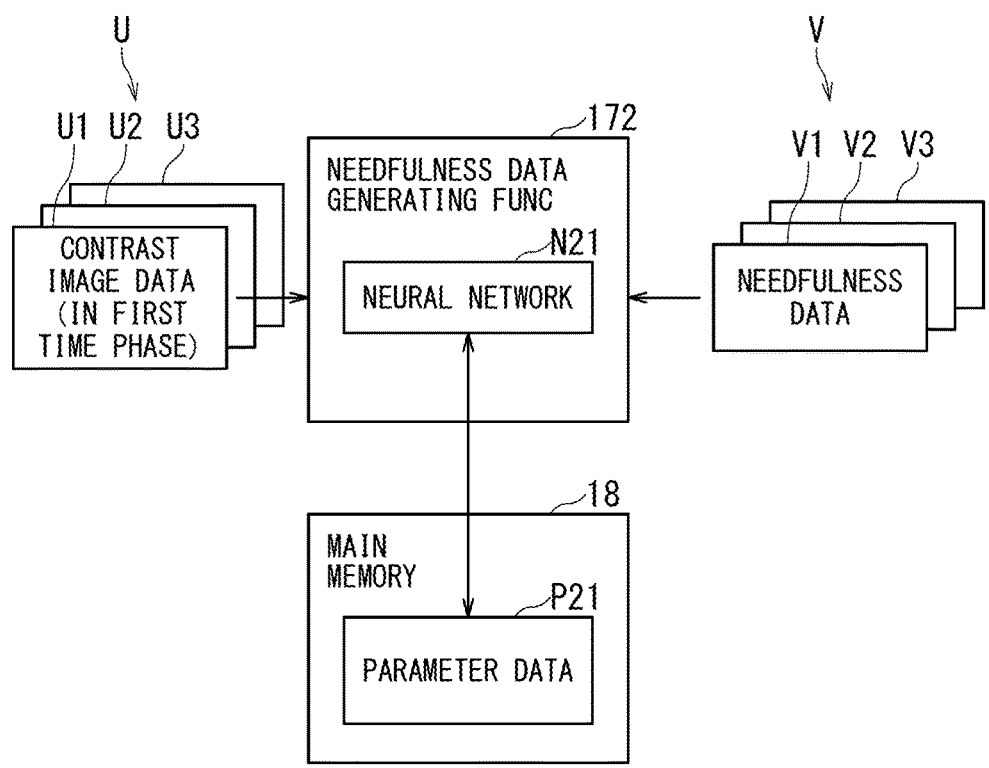
FIG. 7A is an explanatory diagram showing an example of a data flow during learning in the case of the first time phase in the medical image processing apparatus according to the embodiment.
Figure 7B:
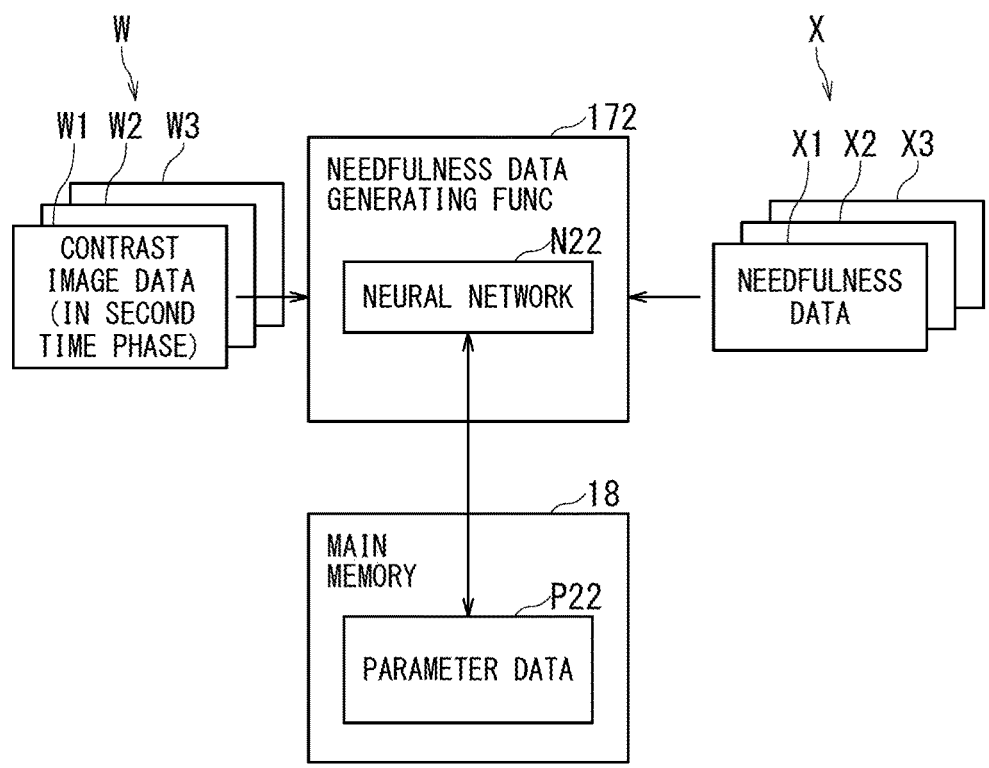
FIG. 7B is an explanatory diagram showing an example of a data flow during learning in the case of the second time phase in the medical image processing apparatus according to the embodiment.

FIG. 7A is an explanatory diagram showing an example of a data flow during learning in the case of the first time phase. FIG. 7B is an explanatory diagram showing an example of a data flow during learning in the case of the second time phase.

FIG. 7A will be described. The needfulness data generating function 172 inputs a large number of contrast image data generated in the first time phase as training data and performs learning, thereby sequentially updates the parameter data P21. The training data includes a set of contrast image data U1, U2, U3, . . . generated in the first time phase as training input data, and needfulness data V1, V2, V3, . . . . The contrast image data U1, U2, U3, . . . generated in the first time phase constitutes the training input data group U. The needfulness data V1, V2, V3, . . . for storage constitutes the training output data group V.

The needfulness data generating function 172 updates the parameter data P21 every time the training data is input such that the result of processing the contrast image data U1, U2, U3, . . . generated in the first time phase by the neural network N21 approaches the needfulness data V1, V2, V3, . . . regarding storage. That is, the needfulness data generating function 172 does so-called learning. Generally, when the rate of change of the parameter data P21 converges within the threshold value, the learning is determined to be completed.

Hereinafter, the parameter data P21 after learning is particularly referred to as learned parameter data P21' (shown in FIG. 8A).

Figure 8A:
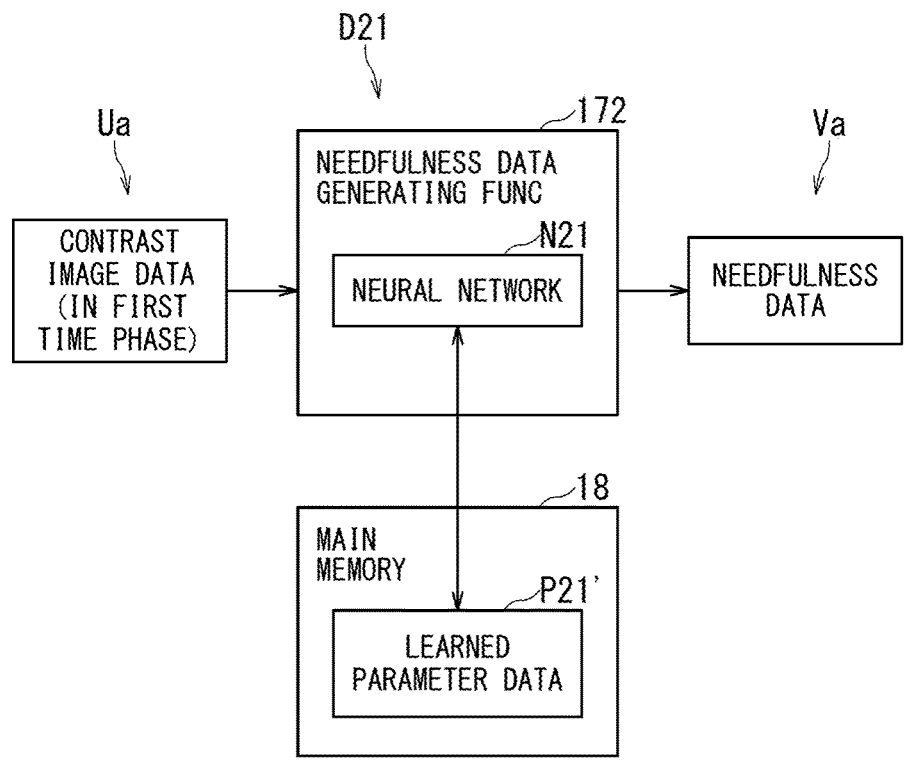
FIG. 8A is an explanatory diagram showing an example of a data flow during operation in the case of the first time phase in the medical image processing apparatus according to the embodiment.

It should be noted that the type of training input data and the type of input data during operation shown in FIG. 8A should match. For example, if the input data during operation is contrast image data of the subject, the training input data group U during learning is also set as contrast image data.

Further, the "image data" includes raw data generated by a medical image generating apparatus such as an ultrasonic diagnostic apparatus. That is, the input data of the neural network N21 may be raw data before the scan conversion.

FIG. 7B will be described. Similar to the case of FIG. 7A, the needfulness data generating function 172 performs learning by inputting a large number of contrast image data generated in the second time phase as training data, thereby sequentially updates the parameter data P22.

Figure 8B:
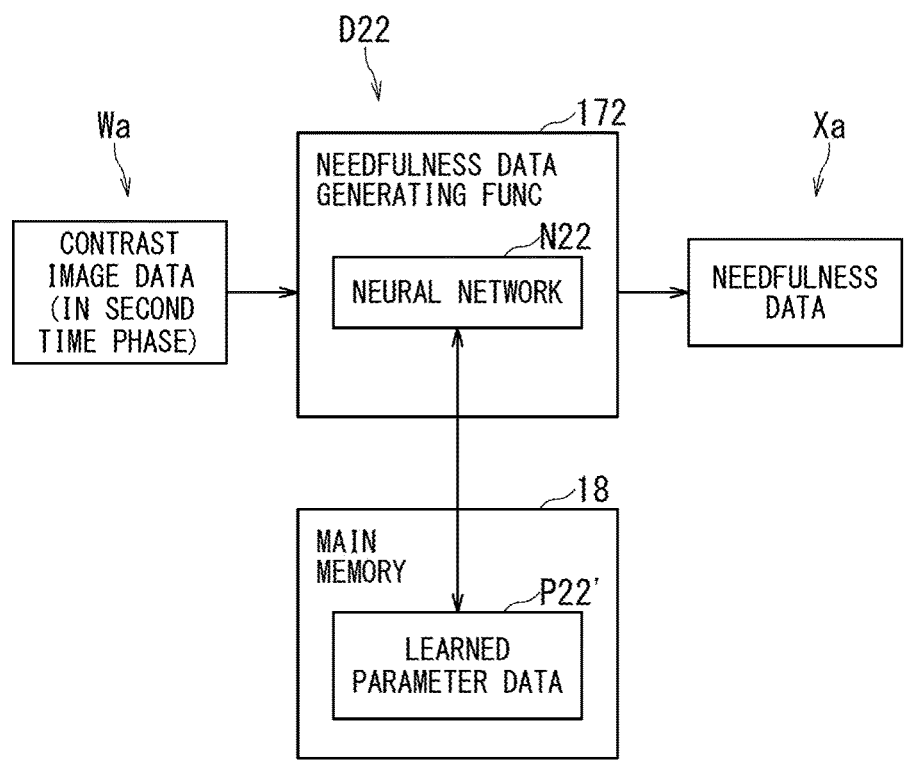
FIG. 8B is an explanatory diagram showing an example of a data flow during operation in the case of the second time phase in the medical image processing apparatus according to the embodiment.

FIG. 8A is an explanatory diagram showing an example of a data flow during operation in the case of the first time phase. FIG. 8B is an explanatory diagram showing an example of a data flow during operation in the case of the second time phase.

FIG. 8A will be described. In operation, the needfulness data generating function 172 acquires the time phase corresponding to the target frame (e.g., the latest frame) of the subject to be diagnosed. Then, the needfulness data generating function 172 inputs the contrast image data Ua to the learned model D21 when determining that the time phase band is the first time phase band, thereby outputs the needfulness data Va regarding the storage of the contrast image data of the subject using the learned parameter data P21'.

The neural network N21 and the learned parameter data P21' form a learned model D21. The neural network N21 is stored in the main memory 18 in the form of a program. The learned parameter data P21' may be stored in the main memory 18, or may be stored in a storage medium connected to the ultrasonic diagnostic apparatus 10 via the network N. In this case, the needfulness data generating function 172 realized by the processor of the processing circuitry 17 reads the learned model D21 from the main memory 18 and executes it, thereby generates needfulness data regarding the storage of the contrast image data based on the contrast image data. The learned model D21 may be constructed by an integrated circuit such as ASIC and FPGA.

It should be noted that the needfulness data Va may be, for example, data indicating either necessity "1" or unnecessity "0". The needfulness data Va is output by the learned model D21 including the needfulness data generating function 172, and relates to storage of contrast image data of the subject.

Further, as the input data, in addition to the contrast image data, identification information including at least one of the height, weight, medical history, and medical history of relatives of the imaging region may be used.

FIG. 8B will be described. Similar to the case of FIG. 8A, during operation, the needfulness data generating function 172 acquires the time phase corresponding to the target frame (e.g., latest frame) of the subject to be diagnosed. Then, the needfulness data generating function 172 inputs the contrast image data Wa to the learned model D22 when it is determined that the time phase is the second time phase, thereby outputs the needfulness data Xa regarding the storage of the contrast image data of the subject using the learned parameter data P22'.

The contrast image data is not limited to the case of one frame image data. The contrast image data may be dynamic image data for each time phase including multiple consecutive frames. In this case, the dynamic image data related to the first time phase is used as the training input data related to the first time phase, and the dynamic image data Ua related to the first time phase of the subject is input to the learned model D21. In addition, the dynamic image data related to the second time phase is used as training input data related to the second time phase, and the dynamic image data Wa related to the second time phase of the subject is input to the learned model D22. As a result, it is possible to learn dynamic moving of bubbles included in the contrast agent.

Further, the contrast image data may be one dynamic image data including multiple continuous frames and is divided into multiple time phases by an index. In this case, partial image data of the dynamic image related to the first time phase divided by the index is used as the training input data related to the first time phase, and the partial image data Ua of the dynamic image of the subject in the first time phase is input to the learned model D21.

According to the medical image processing apparatus M2, by constructing and operating one learned model for each time phase, in addition to the effect of the medical image processing apparatus M1, it is possible to acquire more accurate storage accuracy.

3. Medical Image Processing Apparatus According to the Third Embodiment

In the above-described first embodiment, the case where one neural network is configured regardless of the time phase has been described. In the second embodiment, the case where one neural network is configured for each time phase has been described. However, it is not limited to those cases.

For example, one neural network may be configured regardless of the classification of tumor categories. That is, the needfulness data generating function 172 inputs the contrast image data of the subject related to each category classification of the tumor with respect to one learned model, thereby generates the needfulness data regarding the storage of the contrast image data of the subject according to each category classification.

For example, one neural network may be configured for each tumor category classification. That is, the needfulness data generating function 172 inputs the contrast image data of the subject to the learned model corresponding to the category classification among the multiple learned models corresponding to the multiple category classifications of the tumor, thereby generates needfulness data regarding the storage of contrast image data of the subject. This case will be described as a medical image processing apparatus M3 (shown in FIGS. 1 and 2) according to the third embodiment.

The configuration and function of the medical image processing apparatus M3 are equivalent to those shown in FIGS. 1 and 2. The operation of the medical image processing apparatus M3 is equivalent to that shown in FIG. 3. Therefore, their description is omitted.

In this case, the needfulness data generating function 172 inputs the contrast image data of the subject in the first category classification to the first learned model, thereby generates needfulness data regarding storage of contrast image data of the subject. The first learned model is for generating needfulness data regarding storage based on the contrast image data in the first category classification of the tumor. On the other hand, the needfulness data generating function 172 inputs the contrast image data of the subject in the second category classification to the second learned model, thereby generates needfulness data regarding storage of contrast image data of the subject. The second learned model is for generating needfulness data regarding storage based on the contrast image data related to the second category classification of the tumor.

It should be noted that the information on the category classification of tumors is, for example, HCC (Hepatocellular Carcinoma), Meta (Metastatic Liver Tumor), Hema (Hepatic Hemangioma), FNH (Focal Nodular Hyperplasia), and the like.

According to the medical image processing apparatus M3 according to the third embodiment, by constructing and operating one learned model D3 for each category classification of tumors, in addition to the effect of the medical image processing apparatus M1, it is possible to acquire a highly accurate storage accuracy by constructing and operating one learned model D3 for each category classification of tumors.

4. First Modification

In the medical image processing apparatuses M1 to M3 according to the above-described first to third embodiments, the case where the training input data or the input to the learned model is the contrast image data or the contrast image data with incidental information such as identification information has been described. However, it is not limited to those cases. At least one of the B-mode image data, the color Doppler image data, and the power Doppler image data may be added to the training input data or the input to the learned model.

The B-mode image data may be so-called B-mode image data generated by imaging that is different from the contrast image data by CHI, or may be fundamental image data or the like generated from the reflected wave data (received signal) of the fundamental wave component and generated in the same scan as the contrast image.

According to the first modification of the medical image processing apparatuses M1 to M3 according to the first to third embodiments, in addition to the effects of the medical image processing devices M1 to M3, it is possible to acquire more accurate diagnostic results.

5. Second Modification

In the above-described first embodiment, the case where the training output data is the needfulness data for storage has been described. However, it is not limited to this case. In addition to the needfulness data, at least one of the time phase data and the definitive diagnostic result data may be added to the training output data. An example of the time phase information will be described in the fourth embodiment described later.

The definitive diagnostic result data may be, for example, data indicating either benign or malignant, may be data indicating which one of the category classifications such as HCC, Meta, Hema, and FNH belongs, or may be data that indicates the likelihood of categorization in percent (e.g., benign x %, or malignant y %). Further, the category classification may be the degree of differentiation (e.g., high differentiation or low differentiation) acquired by further subdividing HCC and the like.

According to the medical image processing apparatuses M1 to M3 (including modifications), it is possible to make a definite diagnosis of a tumor without depending on the experience or subjectivity of an operator such as a doctor, and to shorten the diagnosis time.

6. Medical Image Processing Apparatus According to the Fourth Embodiment

In the above first to third embodiments, the case where the image acquiring function 171 acquires the contrast image data live, and where the needfulness data generating function 172 generates the needfulness data of each contrast image data in substantially real time has been described. That is, this is the case where the time phase data of each contrast image data is known. Here, a case where the time phase data of each contrast image data is unknown will be described as the medical image processing apparatus 54 (shown in FIGS. 1 and 2) according to the fourth embodiment. The concept when the time phase data of each contrast image data is unknown may include a case where the image acquiring function 171 acquires multiple contrast image data from the image memory 15 after imaging, and where the needfulness data generating function 172 generates the needfulness data in a post process (post processing) based on the multiple contrast image data, or may include the case where the needfulness data generating function 172 generates the needfulness data in substantially real time.

The needfulness data generating function 172 inputs the contrast image data to the learned model to generate the time phase data. The learned model is for generating the time phase data classified by the contrast state of the lesion area using the contrast agent based on the contrast image data acquired by the image acquiring function 171.

Figure 9A:
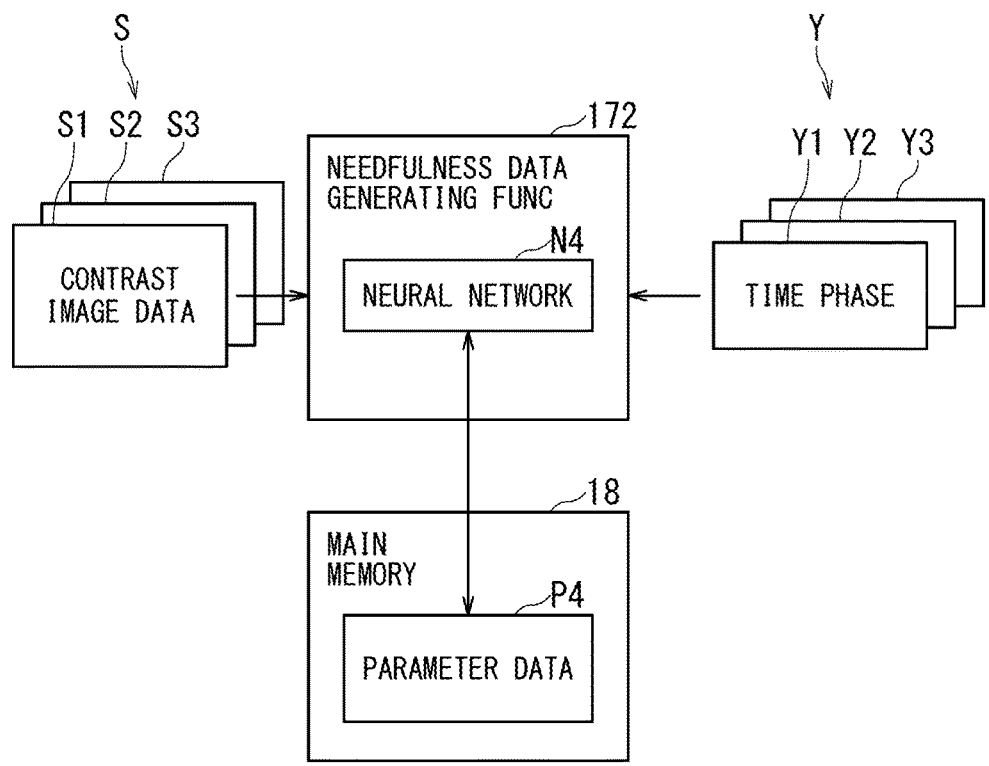
FIG. 9A is an explanatory diagram showing an example of a data flow during operation in the medical image processing apparatus according to the embodiment.

FIG. 9A is an explanatory diagram showing an example of a data flow during operation.

FIG. 9A will be described. The needfulness data generating function 172 performs learning by inputting a large number of contrast image data related to a predetermined frame as training data, thereby sequentially updates the parameter data P4. The training data is a combination of the contrast image data S1, S1, S3, . . . of each frame as the training input data and the time phase data Y1, Y2, Y3, . . . . The contrast image data S1 constitutes a training input data group S. The time phase data Y1, Y2, Y3, . . . constitutes a training output data group Y.

The needfulness data generating function 172 updates the parameter data P4 each time the training data is input such that the result of processing the contrast image data S1, S2, S3, . . . by the neural network N4 should approach the time phase data Y1, Y2, Y3, . . . regarding storage. That is, the needfulness data generating function 172 performs so-called learning. Generally, when the change rate of the parameter data P4 converges within the threshold value, the learning is determined to completed. Hereinafter, the parameter data P4 after learning will be particularly referred to as learned parameter data P4'.

Figure 9B:
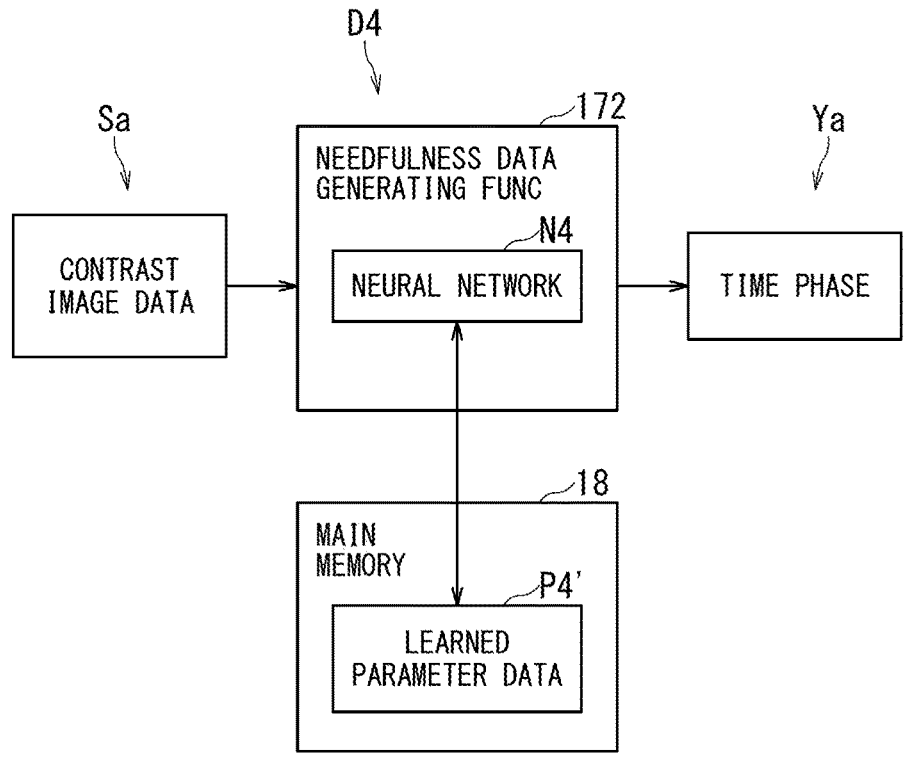
FIG. 9B is an explanatory diagram showing an example of a data flow during operation in the case of the first time phase in the medical image processing apparatus according to the embodiment.

It should be noted that the type of training input data and the type of input data during operation shown in FIG. 9B should match. For example, when the input data during operation is the contrast image data of the subject, the training input data group S during learning is also the contrast image data.

Further, the "image data" includes raw data generated by a medical image generating apparatus such as an ultrasonic diagnostic apparatus. That is, the input data of the neural network N4 may be raw data before the scan conversion.

FIG. 9B will be described. As in the case of FIG. 9A, the needfulness data generating function 172 sequentially updates the parameter data P4 by performing learning by inputting a large number of contrast image data as training data.

FIG. 9B is an explanatory diagram showing an example of a data flow during operation in the case of the first time phase.

FIG. 9B will be described. In operation, the needfulness data generating function 172 inputs the contrast image data Sa corresponding to the target frame of the subject to be diagnosed, thereby outputs the time phase data Ya regarding the storage of the contrast image data of the subject using the learned parameter data P4'.

The neural network N4 and the learned parameter data P4' constitute a learned model D4. The neural network N4 is stored in the main memory 18 in the form of a program. The learned parameter data P4' may be stored in the main memory 18 or may be stored in a storage medium connected to the ultrasonic diagnostic apparatus 10 via the network N. In this case, the needfulness data generating function 172 realized by the processor of the processing circuitry 17 reads the learned model D4 from the main memory 18 and executes it, thereby generates time phase data of the contrast image data based on the contrast image data. The learned model D4 may be constructed by an integrated circuit such as ASIC or FPGA.

In addition to the contrast image data, identification information including at least one of height, weight, medical history, and medical history of relatives may be used as the input data. This is to improve the accuracy of judgment by the needfulness data generating function 172.

As a result, the time phase data of each contrast image data is known. The needfulness data generating function 172 inputs the contrast image data of the subject to the learned model, as described in the first to third embodiments, thereby generates information on the necessity of storing the contrast image data of the subject. The learned model is for generating needfulness data based on multiple contrast image data and their time phase data. That is, the fourth embodiment can be applied to any of the first to third embodiments.

According to the medical image processing apparatus M4, not only the elapsed time from the start of contrast agent injection but also the time phase data based on the contrast image data can be estimated. Further, by applying the estimated time phase data to the first to third embodiments, it is possible to make the definite diagnosis of the tumor in the post process after the completion of imaging, without depending on the experience or subjectivity of an operator such as a doctor, and shorten the diagnosis time.

7. Medical Image Processing Apparatus According to the Fifth Embodiment

The above-described first to fourth embodiments are characterized by setting time phase data of each contrast image data and setting needfulness data of each contrast image data. In the present embodiment, the diagnostic result data of the subject regarding the tumor is generated based on the time phase data or the needfulness data of each of the contrast image data described above. This case will be described as a medical image processing apparatus M5 (shown in FIG. 1) according to the fifth embodiment.

The configuration of the medical image processing apparatus M5 according to the fifth embodiment is the same as that shown in FIG. 1. Therefore, this description will be omitted.

Figure 10:
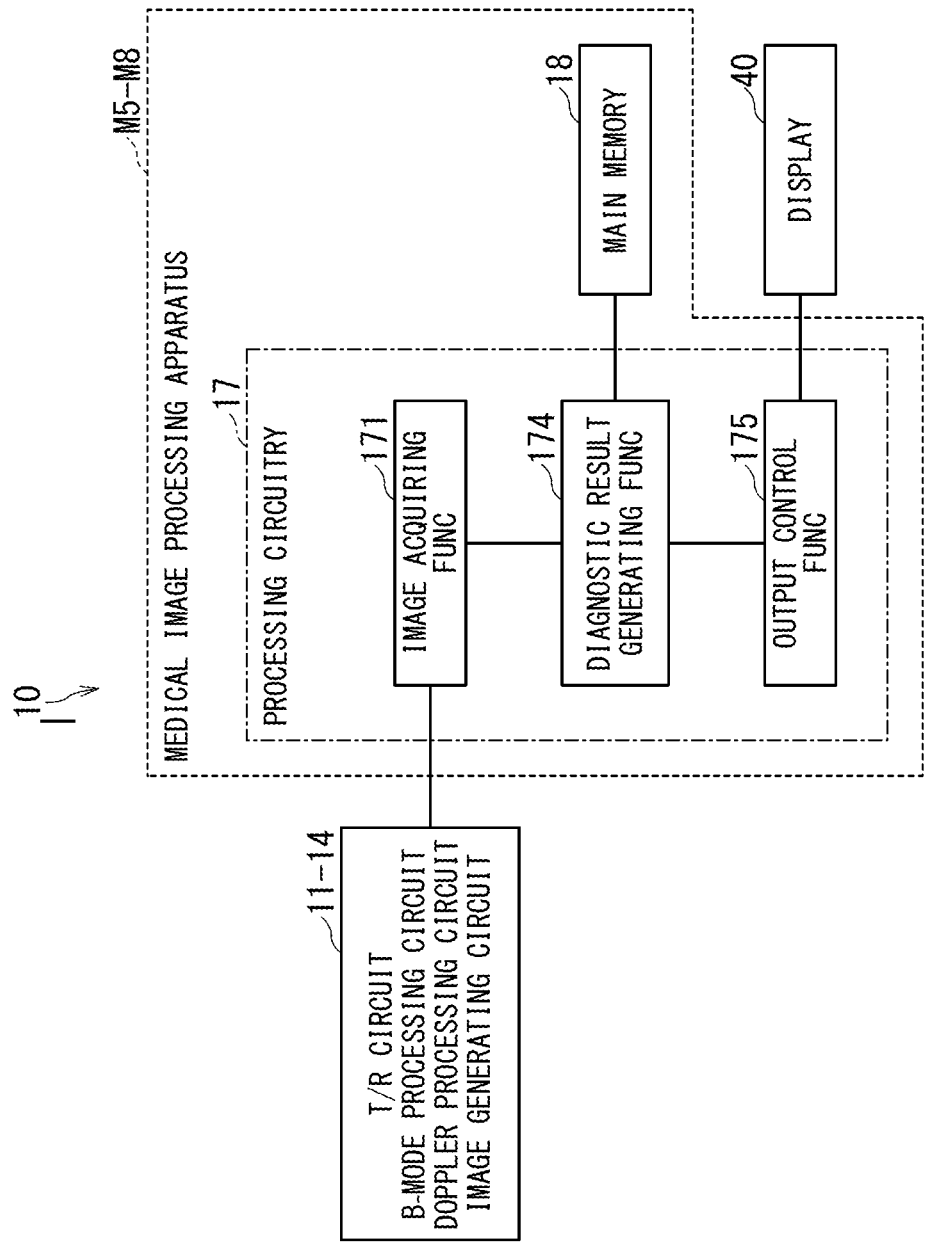
FIG. 10 is a block diagram showing functions of the medical image processing apparatus according to the embodiment.

FIG. 10 is a block diagram showing functions of the medical image processing apparatus M5.

The processing circuitry 17 reads and executes a program stored in the main memory 18 or directly installed in the processing circuitry 17, thereby realizes an image acquiring function 171, a diagnostic result generating function 174, and an output control function 175. Hereinafter, a case where the functions 171, 174, and 175 function as software will be described as an example. All or part of the functions 171, 174, and 175 may be provided in the ultrasonic diagnostic apparatus 10 as a circuit such as an ASIC.

In FIG. 10, the same members as those shown in FIG. are designated by the same reference numerals and the description thereof will be omitted.

The diagnostic result generating function 174 includes a function of inputting multiple contrast image data of the subject in multiple time phases to the learned model for generating diagnostic result data regarding the tumor based on the multiple contrast image data related to different time phases, thereby generating data related to the type of lesion area (e.g., diagnostic result data of a subject regarding a tumor). The diagnostic result generating function 174 is one example of a diagnostic result generating unit.

The output control function 175 includes a function of displaying the diagnostic result data generated by the diagnostic result generating function 174 on the display 40 or outputting a voice through a speaker (not shown) to present diagnostic result data to an operator such as a doctor. The output control function 175 is one example of an output control unit.

Details of the functions 171, 174, and 175 will be described with reference to FIGS. 11 to 17.

Subsequently, the operation of the ultrasonic diagnostic apparatus 10 will be described. Here, a combination of two (or three) different time phases as n (n=2, 3, 4, . . . ) different time phases will be described as an example. However, it is not limited to this case. The multiple different time phases may be, for example, a combination of four or more different time phases.

Figure 11:
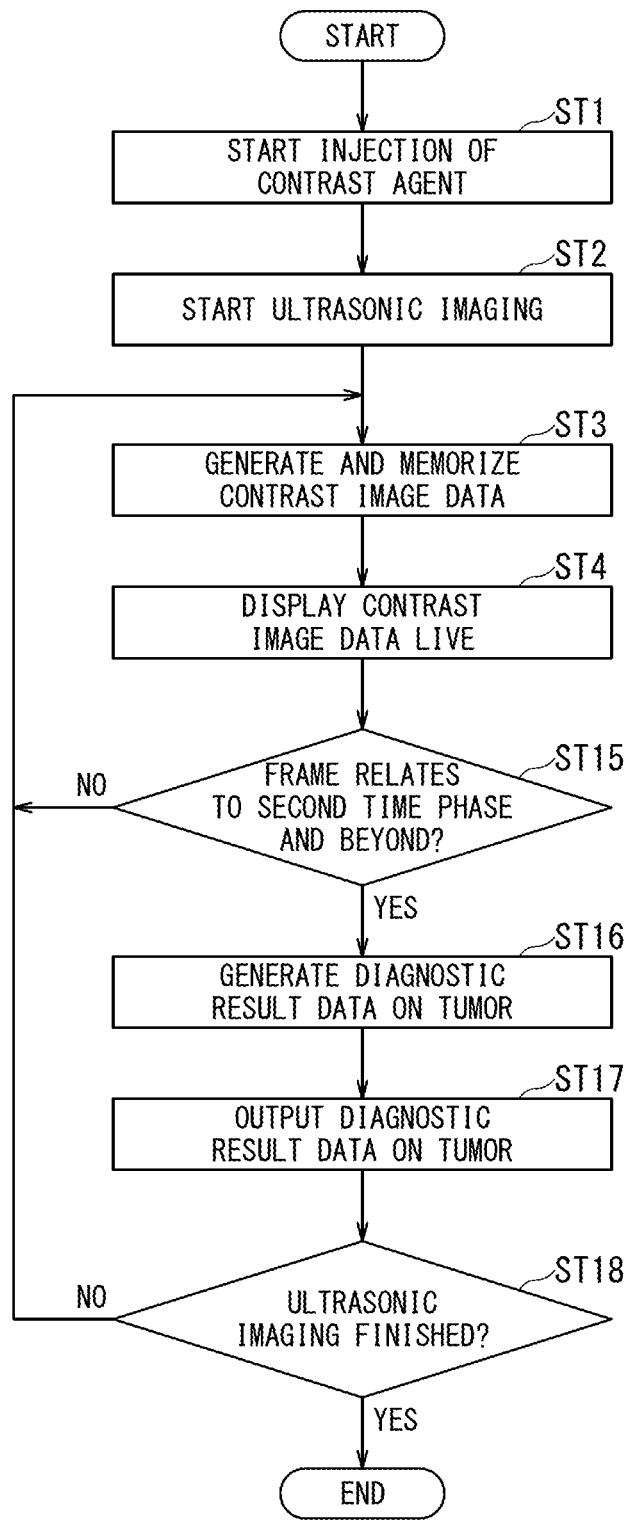
FIG. 11 is a diagram showing an operation of the ultrasonic diagnostic apparatus as a flowchart according to the embodiment.

FIG. 11 is a diagram showing an operation of the ultrasonic diagnostic apparatus 10 as a flowchart. In FIG. 11, the reference symbols with the numbers attached to "ST" indicate the steps of the flowchart.

In FIG. 11, the same steps as those in FIG. 3 are designated by the same reference numerals and the description thereof will be omitted.

Subsequent to step ST4, the diagnostic result generating function 174 determines whether or not the time phase of the contrast image data generated in step ST3 relates to the second and subsequent time phases after the injection of the contrast agent (step ST15). After the injection of the contrast agent, the tumor is classified into multiple time phases depending on the degree of the tumor image by the contrast agent. For example, when the imaging region is the liver, it is classified into time phases such as an early vascular phase, an arterial predominant phase, a portal predominant phase, and a post vascular phase according to the elapsed time from the start of injection of the contrast agent.

If it is determined as "NO" in step ST15, that is, if it is determined that the time phase of the contrast image data generated in step ST3 is related to the first time phase (e.g., the early vascular phase) after the injection of the contrast agent, the image acquiring function 171 controls the image generating circuit 14 and the like to generate contrast image data for a next frame and stores it in the image memory 15 (step ST3).

On the other hand, if it is determined as "YES" in step ST15, that is, if it is determined that the time phase of the contrast image data generated in step ST3 is related to the second and subsequent time phases (e.g., the arterial predominant phase) after the injection of the contrast agent, the diagnostic result generating function 174 generates diagnostic result data regarding the tumor based on the latest frame contrast image data generated in step ST3 and the past frame contrast image data stored in the image memory 15 (step ST16). Here, the contrast image data of the past frame is image data of a frame related to a time phase different from the time phase of the latest frame.

In the description of the fifth embodiment, the diagnostic result generating function 174 performs a processing of generating the diagnostic result data regarding the tumor on the basis of the combination of two contrast image data respectively generated in two different time phases. This processing may be, for example, a processing using a lookup table (LUT). The LUT associates a combination of two contrast image data respectively generated in two time phases with the diagnostic result data regarding the tumor. Further, this processing may be a processing using machine learning. Further, this processing may be a processing using deep learning using the multilayer neural network such as CNN or convolutional deep belief network as machine learning.

In the description of the fifth embodiment, the diagnostic result generating function 174 includes the neural network N5. Then, the deep learning is used to generate the diagnostic result data regarding the tumor on the basis of the combination of the two contrast image data (one contrast image data related to the first time phase and one contrast image data related to the second time phase) generated in the two phases.

Figures 12A, 12B:
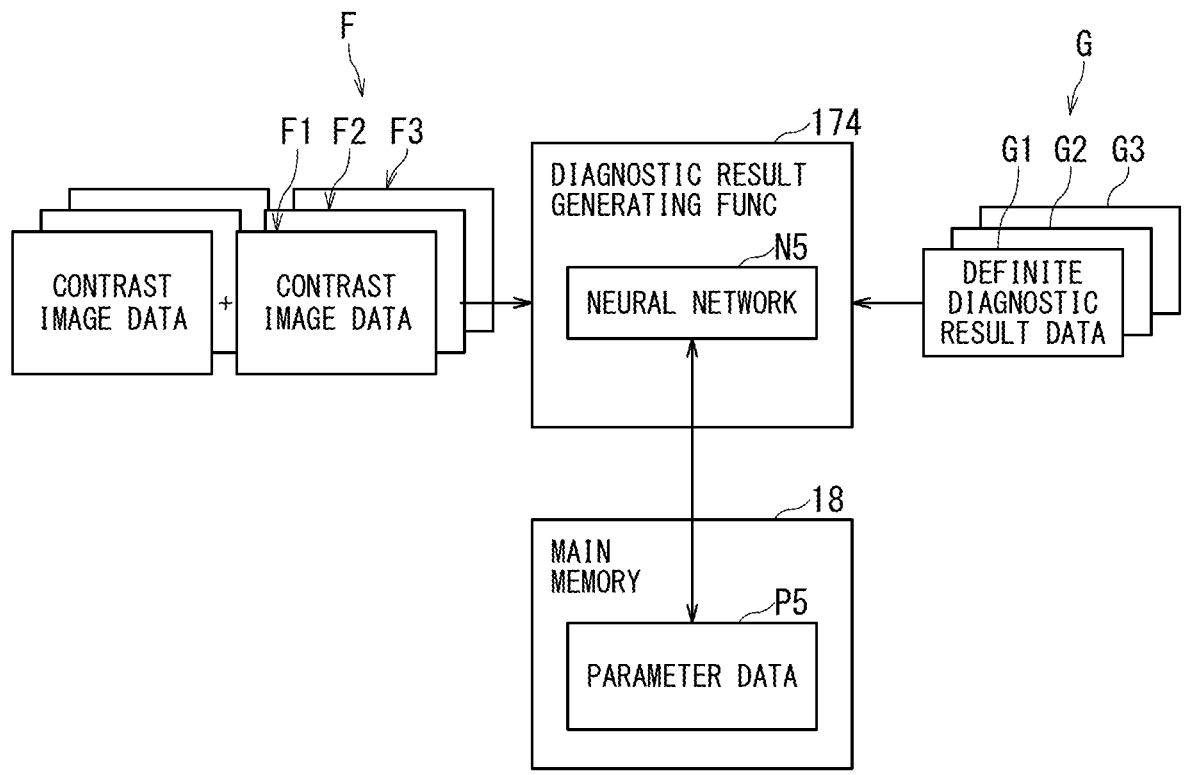
FIG. 12A is an explanatory diagram showing an example of a data flow during learning in the medical image processing apparatus according to the embodiment.
FIG. 12B is a diagram showing an example of training data as a table in the medical image processing apparatus according to the embodiment.

FIG. 12A is an explanatory diagram showing an example of a data flow during learning. FIG. 12B is a diagram showing an example of training data as a table.

The diagnostic result generating function 174 sequentially updates the parameter data P5 by receiving a large number of training data and performing learning. The training data is composed of combinations F1, F1, F3, . . . of two contrast image data generated in two time phases as training input data and ideal diagnostic results G1, G2, G3, . . . . The combinations F1, F2, F3, . . . of the two contrast image data generated in each of the two time phases constitutes the training input data group F. The ideal diagnostic results G1, G2, G3, . . . constitute the training output data group G. Each of ideal diagnostic results G1, G2, G3, . . . is preferably a definite diagnostic result regarding the tumor. Each of the definite diagnostic results is determined by taking out the tissue from the imaging target person of each of the combinations F1, F2, F3, . . . corresponding to each of the ideal diagnostic results G1, G2, G3, . . . and examining it.

The diagnostic result generating function 174 updates the parameter data P5 each time the training data is input such that the result of processing the combinations F1, F2, F3, . . . of the two contrast image data respectively generated in the two time phases with the neural network N5 approaches the definite diagnostic combinations G1, G2, G3, . . . regarding the tumor. That is, the diagnostic result generating function 174 performs so-called learning. Generally, when the change rate of the parameter data P5 converges within the threshold value, the learning is determined to be completed. Hereinafter, the learned parameter data P5 is particularly referred to as learned parameter data P5' (shown in FIG. 13).

Figure 13:
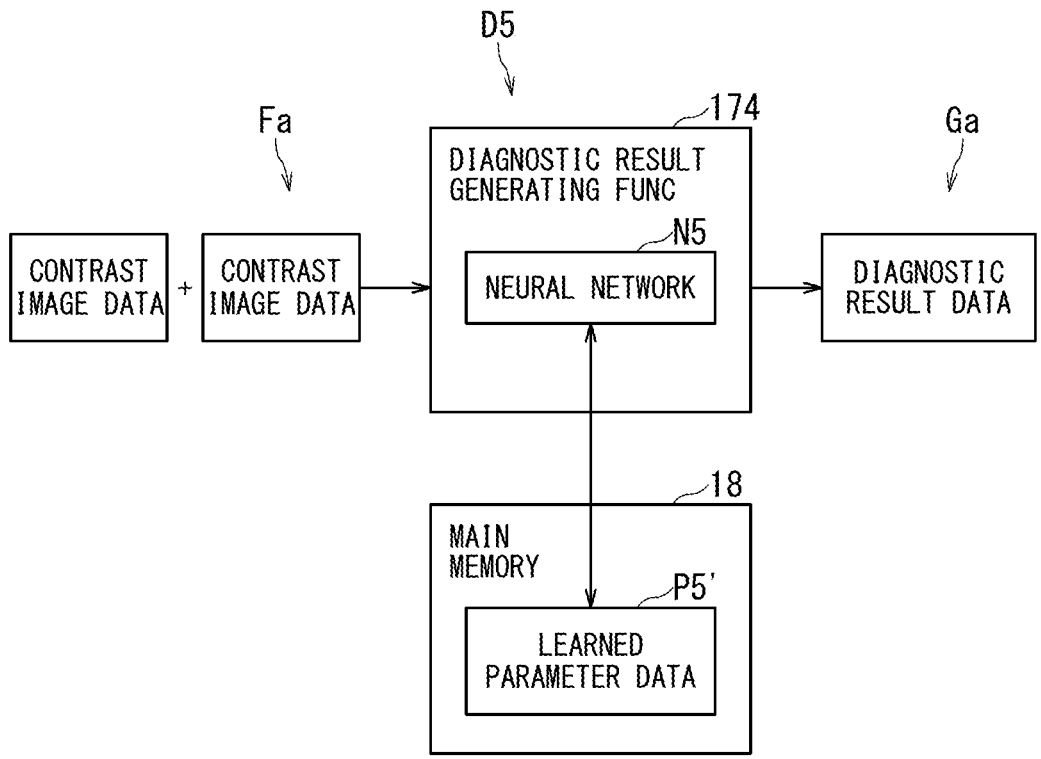
FIG. 13 is an explanatory diagram showing an example of a data flow during operation in the medical image processing apparatus according to the embodiment.

It should be noted that the type of training input data and the type of input data during operation shown in FIG. 13 should match. For example, when the input data at the time of operation is the contrast image data of the subject, the training input data group F at the time of learning is also the contrast image data.

Further, the "image data" includes raw data generated by a medical image generating apparatus such as an ultrasonic diagnostic apparatus. That is, the input data of the neural network N5 may be raw data before the scan conversion.

FIG. 13 is an explanatory diagram showing an example of a data flow during operation.

During operation, the diagnostic result generating function 174 inputs to the learned model D5 the combination Fa of the two contrast image data generated in each of the two time phases of the subject to be diagnosed, thereby outputs the diagnostic result data Ga regarding the tumor of the subject using the learned parameter data P5'.

The neural network N5 and the learned parameter data P5' constitute a learned model D5. The neural network 1\15 is stored in the main memory 18 in the form of a program. The learned parameter data P5' may be stored in the main memory 18 or a storage medium connected to the ultrasonic diagnostic apparatus 10 via the network N. In this case, the diagnostic result generating function 174 realized by the processor of the processing circuitry 17 reads the learned model D5 from the main memory 18 and executes it, thereby generates the diagnostic result data regarding the tumor based on the combination of the two contrast image data generated in the two time phases. The learned model D5 may be constructed by an integrated circuit such as ASIC and FPGA.

The diagnostic result data Ga regarding the tumor of the subject output by the learned model D5 including the diagnostic result generating function 174 may be data indicating either benign or malignant, may be data indicating which one of the category classifications such as HCC (Hepatocellular Carcinoma), Meta (Metastatic Liver Tumor), Hema (Hepatic Hemangioma), and FNH (Focal Nodular Hyperplasia), or may be data (e.g., benign x % or malignant y %) indicating the possibility of category classification in percent. Further, the category classification may be the degree of differentiation (e.g., high differentiation or low differentiation) acquired by further subdividing HCC and the like.

Further, as input data, in addition to the combination of two contrast image data, identification information including at least one of the height, weight, medical history of a subject to be imaged, and medical history of relatives may be used. This is to improve the accuracy of tumor diagnosis by the diagnostic result generating function 174.

In this case, at the time of learning, the identification information of each imaging target person of the combinations F1, F2, F3, . . . of the two contrast image data is also input to the neural network N5 as training input data. The two contrast image data are generated in the two time phases as the training input data. During operation, the diagnostic result generating function 174 inputs the identification information of the subject with the combinations Fa of the two contrast image data to the learned model D5 read from the main memory 18, thereby outputs the diagnostic result data Ga regarding the tumor of the subject. The two contrast image data are generated in the two time phases of the subject to be diagnosed. The combination of two contrast image data generated in each of the two time phases and the identification information of the person to be imaged are used as the input data. As a result, the learned parameter data P5' that has been learned according to the type of the person to be imaged is generated. In such manner, the diagnostic accuracy can be improved as compared with the case where only the combination of two contrast image data generated in each of the two time phases is used as the input data.

Returning to the explanation of FIG. 11, the output control function 175 displays the diagnostic result data generated in step ST16 on the display 40 (step ST17). Alternatively, the output control function 175 presents the diagnostic result data to an operator such as a doctor by outputting a voice through a speaker (not shown).

Figure 14:
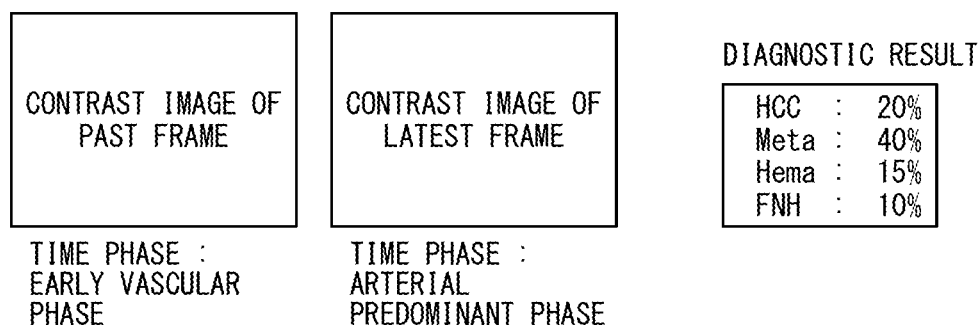
FIG. 14 is a diagram showing a display example of the diagnostic result in the medical image processing apparatus according to the embodiment.

FIG. 14 is a diagram showing a display example of the diagnostic result.

As shown in FIG. 14, a display screen includes an image based on the contrast image data of the latest frame, an image based on the contrast image data of the past frame combined with the image, and the diagnostic result data which is the output of the diagnostic result generating function 174. The display screen includes data indicating the possibility of categorization in percent as a diagnostic result.

Returning to the description of FIG. 11, the image acquiring function 171 determines whether to finish the ultrasonic imaging started in step ST2 (step ST18).

If it is determined as "NO" in step ST18, that is, if it is determined that the ultrasonic imaging started in step ST2 is not to be finished, the image acquiring function 171 controls the image generating circuit 14 and the like, and generates contrast image data for a next frame and stores it in the image memory 15 (step ST3). That is, the ultrasonic imaging is continued.

On the other hand, if it is determined as "YES" in step ST18, that is, if it is determined that the ultrasonic imaging started in step ST2 is to be finished, the image acquiring function 171 determines that the operator has given a finish instruction via the input interface 30, and finishes the ultrasonic imaging.

That is, according to the flowchart shown in FIG. 11, the ultrasonic diagnostic apparatus 10 repeats the setting of steps ST3, ST4, ST15 to ST18 in the second and subsequent time phases, thereby can generate and display the diagnostic result data regarding the tumor for each frame.

The contrast image data is not limited to the case of one frame image data. The contrast image data may be dynamic image data composed of multiple consecutive frames. In this case, a combination of two dynamic image data is used as training input data, and the combination Fa of the two dynamic image data of the subject to be diagnosed is input to the learned model D5. As a result, it is possible to learn dynamic moving of bubbles included in the contrast agent.

Further, according to the flowchart shown in FIG. 11, the diagnostic result generating function 174 generates the diagnostic result data every time the contrast image data of each continuous frame is generated. However, it is not limited to this case. For example, the diagnostic result generating function 174 may generate the diagnostic result data every time the contrast image data of each frame generated at a constant frame interval is generated, or may generate the diagnostic result data each time the contrast image data of the first frame of each time phase is generated.

According to the medical image processing apparatus M5, it is possible to support definite diagnosis of a tumor based on the multiple contrast image data acquired in the multiple different time phases, so it is possible to make a definite diagnosis of a tumor in real time without depending on the experience or subjectivity of an operator such as a doctor.

8. Medical Image Processing Apparatus According to the Sixth Embodiment

In the above-described fifth embodiment, the case where one neural network is configured regardless of the time phase has been described. That is, this is the case where the diagnostic result generating function 174 inputs the contrast image data of the subject in each time phase to one learned model, thereby generates diagnostic result data of the subject regarding each time phase. However, it is not limited to this case.

For example, one neural network may be configured based on a combination of multiple time phases before a predetermined time phase, and one neural network may be configured based on a combination of multiple time phases before another time phase. That is, the diagnostic result generating function 174 inputs the combination of multiple contrast image data of the subject to a learned model corresponding to the combination of the multiple learned models, thereby generates diagnostic result data of the subject. The multiple learned models correspond to a combination of the multiple contrast image data related to a plurality of time phases. This case will be described as a medical image processing apparatus M6 (shown in FIGS. 1 and 10) according to the sixth embodiment.

The configuration and function of the medical image processing apparatus M6 are equivalent to those shown in FIGS. 1 and 10. The operation of the medical image processing apparatus 146 is equivalent to that shown in FIG. 11. Therefore, their description is omitted.

The diagnostic result generating function 174 shown in FIG. 10 generates the diagnostic result data regarding a tumor based on a combination in step ST16 shown in FIG. 11. The combination is a combination of the latest frame contrast image data generated in step ST3 and the former frame contrast image data stored in the image memory 15.

In the embodiment, the diagnostic result generating function 174 performs processing by distinguishing between the case where the target frame is the first time phase and the case where the target frame is the second time phase following the target time frame. When the target frame is in the first time, the diagnostic result generating function 174 performs a processing of generating diagnostic result data regarding a tumor based on a combination of the n contrast image data corresponding to the n time phases before the first time phase. Then, when the target frame is in the second time, the diagnostic result generating function 174 performs a processing of generating diagnostic result data regarding the tumor based on a combination of the n+1 contrast image data corresponding to the n+1 time phases before the second time phase.

Two lookup tables may be used for this processing. For example, one look up table associates a combination of two contrast image data generated in the two time phases before the first time phase with the diagnostic result data regarding the tumor. The other lookup table associates a combination of three contrast image data generated in each of the three time phases before the second time phase with the diagnostic result data regarding the tumor. Machine learning may be used for this processing. Further, deep learning may be used for this processing. The deep learning uses the multilayer neural network such as CNN or a convolutional deep belief network as machine learning.

In the description of the sixth embodiment, the diagnostic result generating function 174 includes multiple neural networks N6 (e.g., "N61" and "N62" shown in FIGS. 15A and 15B, respectively), and deep learning is used to generate diagnostic result data related to a tumor based on a combination of n contrast image data generated in each of n time phases.

Figure 15A:
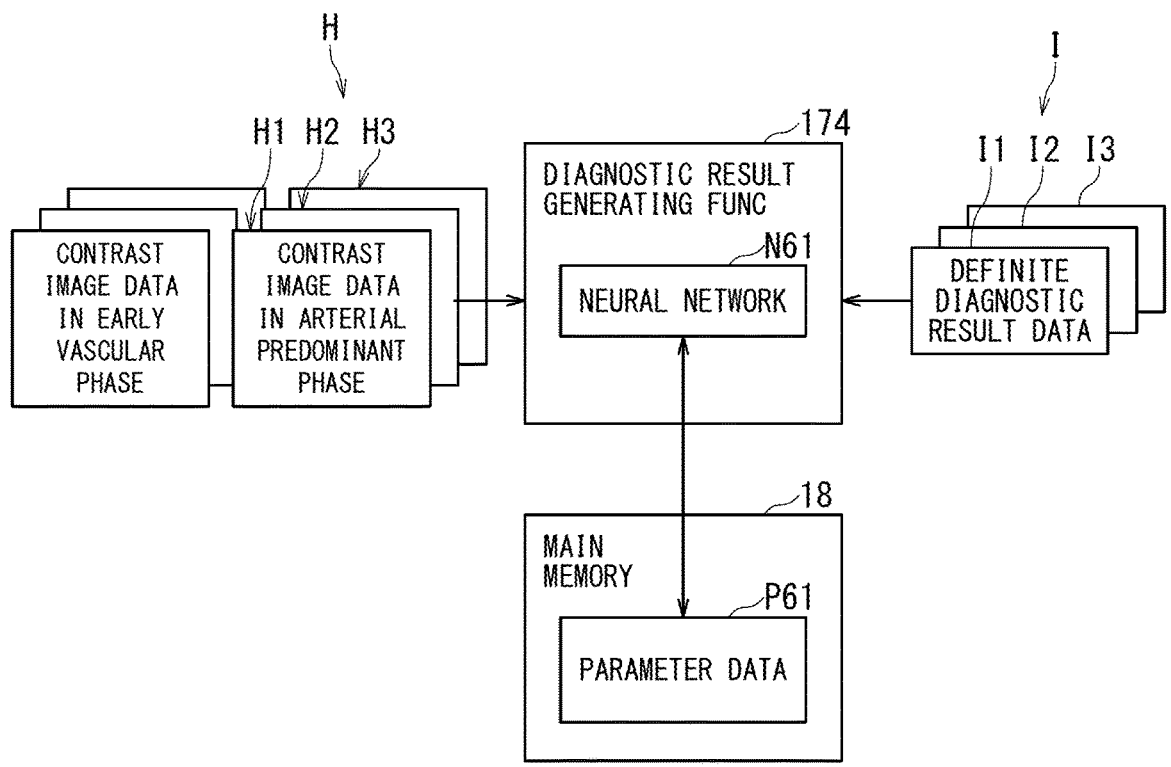
FIG. 15A is an explanatory diagram showing an example of a data flow at the time of learning in the case of combining multiple time phases corresponding to phases before the first time phase in the medical image processing apparatus according to the embodiment.
Figure 15B:
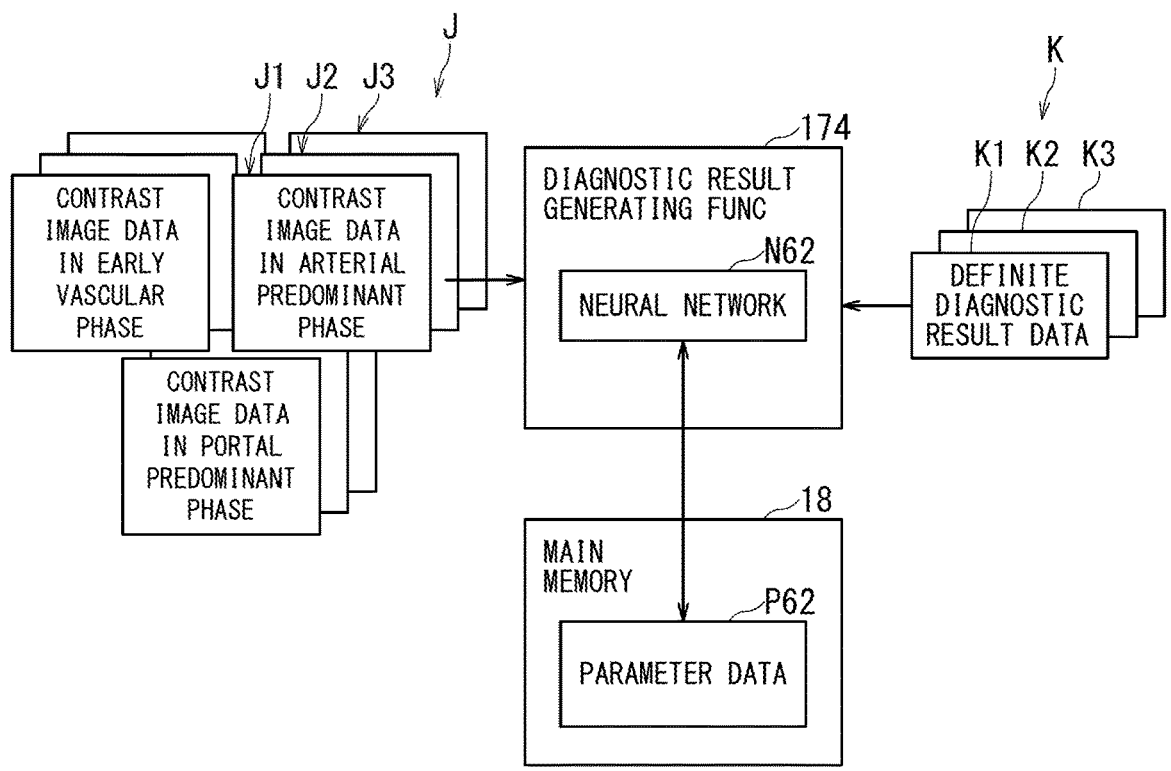
FIG. 15B is an explanatory diagram showing an example of a data flow at the time of learning in the case of combining multiple time phases corresponding to phases before the second time phase in the medical image processing apparatus according to the embodiment.

FIG. 15A is an explanatory diagram showing an example of a data flow at the time of learning in the case of combining multiple time phases corresponding to phases before the first time phase. FIG. 15B is an explanatory diagram showing an example of a data flow at the time of learning in the case of combining multiple time phases corresponding to phases before the second time phase.

FIG. 15A will be described. The diagnostic result generating function 174 sequentially updates the parameter data P61 by receiving a large number of training data before the first time phase, and performing learning. The training data is composed of combinations H1, H2, H3, ... of two contrast image data as training input data and ideal diagnostic results I1, I2, I3, . . . . The two contrast image data are respectively generated in the first time phase, for example, in two early blood vessel and arterial predominant phases before the arterial predominant phase. The combinations H1, H2, H3, ... generated respectively in the two early blood vessel and arterial predominant phases before the arterial predominant phase constitute the training input data group H. The ideal diagnostic results I1, I2, I3, ... constitute the training output data group I. Each of ideal diagnostic results I1, I2, I3, ... is preferably a definite diagnostic result regarding the tumor. Each of the definite diagnostic results is acquired by taking out the tissue from the imaging target person of each of the combinations H1, H2, H3, ... corresponding to each of the ideal diagnostic results I1, I2, I3, ... and examining it.

The diagnostic result generating function 174 updates the parameter data P61 each time the training data is input such that the result of processing by the neural network N61 of the combinations H1, H2, H3, ... of the two contrast image data generated in the two early vascular and arterial predominant phases before the arterial predominant phase approaches the definite diagnostic result I1, I2, I3, ... regarding the tumor. That is, the diagnostic result generating function 174 performs so-called learning. Generally, when the change rate of the parameter data P61 converges within the threshold value, the learning is determined to be completed. Hereinafter, the learned parameter data P61 will be referred to as learned parameter data P61' (shown in FIG. 16A).

Figure 16A:
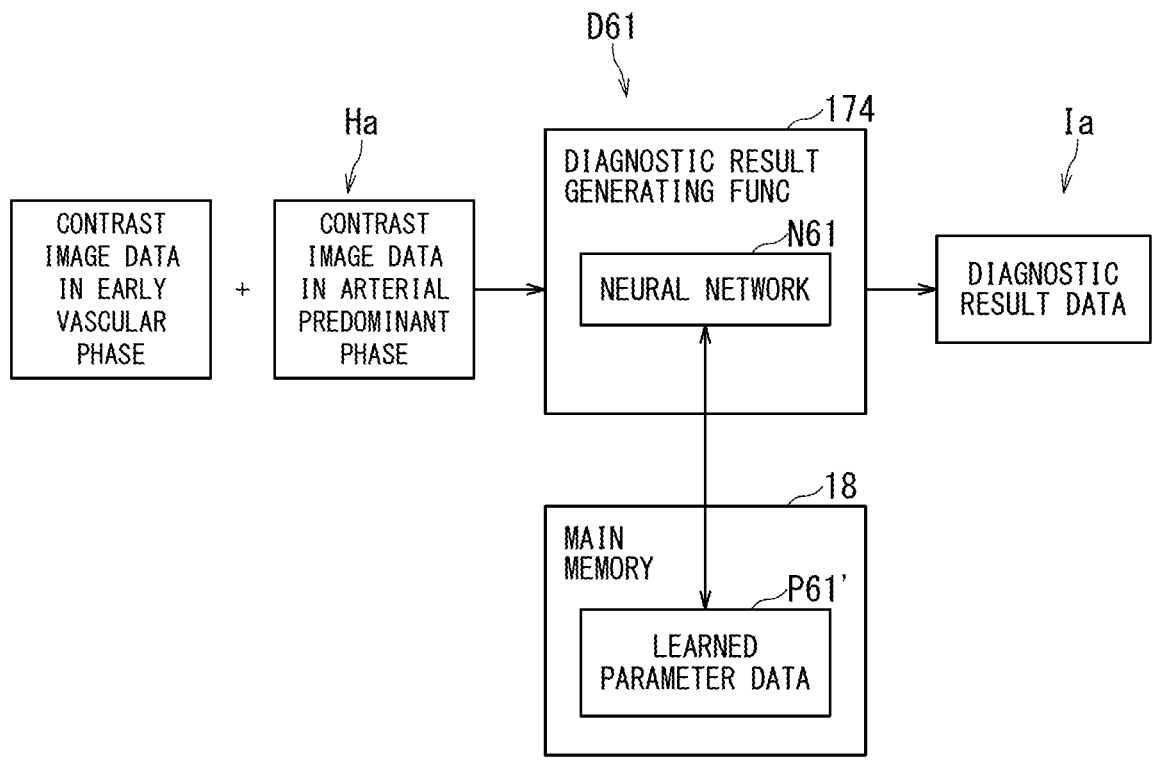
FIG. 16A is an explanatory diagram showing an example of a data flow during operation in the case of combining multiple time phases corresponding to phases before the first time phase in the medical image processing apparatus according to the embodiment.

It should be noted that the type of training input data and the type of input data during operation shown in FIG. 16A should match. For example, when the input data during operation is the contrast image data of the subject, the training input data group H during learning is also the contrast image data.

Further, the "image data" includes raw data generated by a medical image generating apparatus such as an ultrasonic diagnostic apparatus. That is, the input data of the neural network N61 may be raw data before the scan conversion.

FIG. 15B will be described. As in the case of FIG. 15A, the diagnostic result generating function 174 inputs a large number of training data before the second time phase, and performs learning. The diagnostic result generating function 174 sequentially updates the parameter data P62 such that the result of processing the combinations J1, J2, J3, ... of the three contrast image data by the neural network N62 approaches the definite diagnostic results K1, K2, K3, ... regarding the tumor. The three contrast image data are respectively generated in three early blood vessel, arterial predominant and portal predominant phases before the portal predominant phase. That is, the diagnostic result generating function 174 performs so-called learning.

Figure 16B:
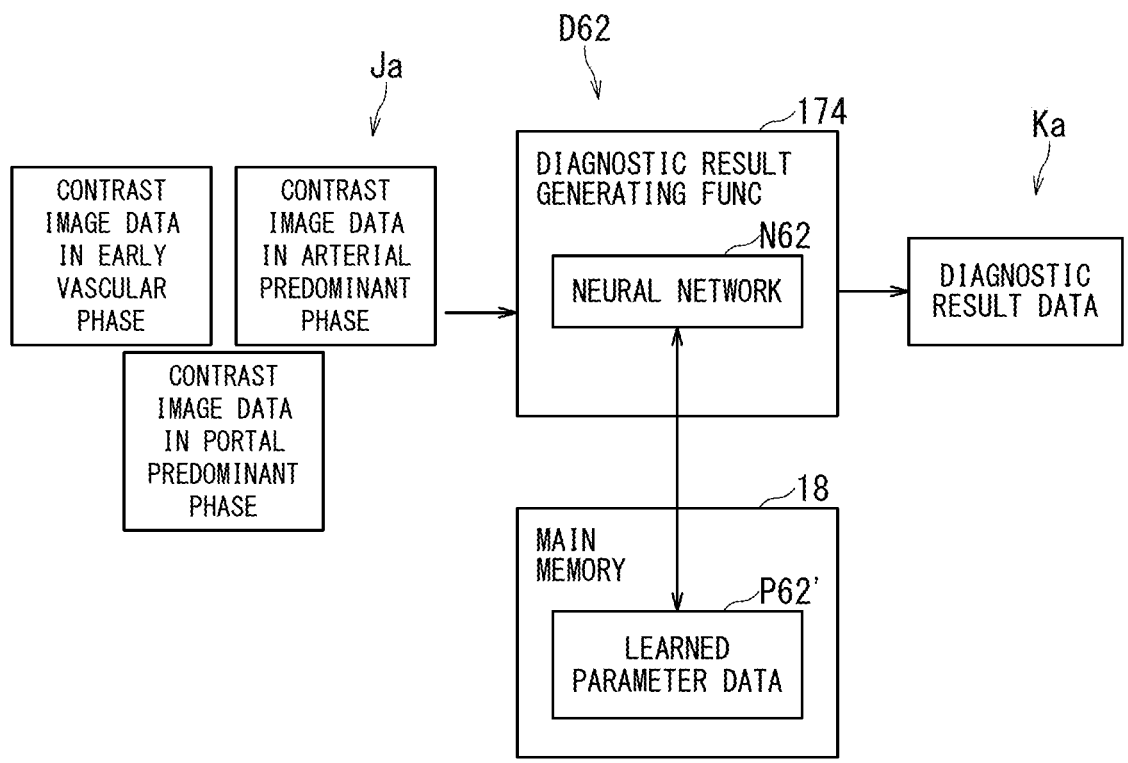
FIG. 16B is an explanatory diagram showing an example of a data flow during operation in the case of combining multiple time phases corresponding to phases before the second time phase in the medical image processing apparatus according to the embodiment.

FIG. 16A is an explanatory diagram showing an example of a data flow during operation in the case of combining multiple time phases corresponding to phases before the first time phase. FIG. 16B is an explanatory diagram showing an example of a data flow during operation in the case of combining multiple time phases corresponding to phases before the second time phase.

FIG. 16A will be described. During operation, the diagnostic result generating function 174 acquires the time phase corresponding to the target frame (e.g., the latest frame) of the subject to be diagnosed. Then, when it is determined that the time phase is the first time phase, for example, the arterial predominant phase, the diagnostic result generating function 174 inputs a combination Ha of two contrast image data to the learned model D61, thereby outputs the diagnostic result data Ia regarding the tumor of the subject using the learned parameter data P61'. The two contrast image data are respectively generated in two early vascular and arterial predominant phases before the arterial predominant phase.

The neural network N61 and the learned parameter data P61' constitute a learned model D61. The neural network N61 is stored in the main memory 18 in the form of a program. The learned parameter data P61' may be stored in the main memory 18, or may be stored in a storage medium connected to the ultrasonic diagnostic apparatus 10 via the network N. In this case, the diagnostic result generating function 174 realized by the processor of the processing circuitry 17 reads the learned model D61 from the main memory 18 and executes it, thereby generates the diagnostic result data regarding the tumor based on the combination of the two contrast image data generated in the two early blood vessel and arterial predominant phases. The learned model D61 may be constructed by an integrated circuit such as ASIC or FPGA.

The diagnostic result data Ia regarding the tumor of the subject output by the learned model D61 including the diagnostic result generating function 174 may be data indicating either benign or malignant, may be data indicating which of the category classifications such as HCC, Meta, Hema, and FNH belongs, or may be data indicating the multiple category classification as a percentage (e.g., benign x % or malignant y %). Further, the category classification may be the degree of differentiation (e.g., high differentiation or low differentiation) obtained by further subdividing HCC and the like.

In addition to the contrast image data, identification information including at least one of height, weight, medical history, and medical history of relatives may be used as the input data. This is to improve the accuracy of tumor diagnosis by the diagnostic result generating function 174.

FIG. 16B will be described. As in the case of FIG. 16A, during operation, the diagnostic result generating function 174 acquires the time phase band corresponding to the target frame (e.g., latest frame) of the subject to be diagnosed. Then, when it is determined that the time phase is the second time phase, for example, the portal vein dominant phase, the diagnostic result generating function 174 inputs a combination Ja of three contrast image data to the learned model D62, thereby outputs the diagnostic result data Ka regarding the tumor of the subject using the learned parameter data P62'. The three contrast image data are generated in three early vascular, arterial predominant and portal predominant phases, respectively.

In the medical image processing apparatus 146, the combination of multiple time phases is classified into two or three, and the neural network is configured for each. However, it is not limited to this case. For example, different neural networks may be configured for combinations of four or more time phases. Alternatively, one neural network may be constructed based only on the characteristic time phase combinations.

Regarding the former, for example, one neural network is configured by a combination of one early blood vessel phase and one arterial dominant phase, one neural network is constructed by a combination of one early vascular phase, one arterial predominant phase, and one portal predominant phases, and one neural network is constructed by a combination of one early vascular phase, one arterial predominant phase, one portal predominant phase, and one post vascular phase. When the time phase corresponding to the target frame (e.g., the latest frame) of the subject to be diagnosed has the arterial predominant phase, the neural network, based on the combination of one early blood vessel phase and one arterial predominant phase, is used. When the time phase advances and the time phase corresponding to the target frame is to be the portal predominant phase, the neural network, based on the combination of one early vascular phase, one arterial predominant phase and one portal predominant phase, is used. When the time phase further advances and the time phase corresponding to the target frame is to be the post vascular phase, the neural network, based on the combination of one early vascular phase, one arterial dominant phase, one portal predominant phase, and one post vascular phase, is used.

As a result, the number of input images increases as the time phase from the start of injection of the contrast agent increases, and the applied neural network changes in real time.

Needless to say, the diagnostic result data of the subject generated in the sixth embodiment may be output with the diagnostic result data of the subject generated in the fifth embodiment.

Furthermore, the contrast image data is not limited to the case of one frame image data. The contrast image data may be dynamic image data for each time phase, which is composed of multiple consecutive frames. In this case, the combination of the dynamic image data related to the early vascular phase and the dynamic image data related to the arterial predominant phase is used as the first training input data, so the combination Ha of the dynamic image data related to the early vascular phase and the dynamic image data related to the arterial predominant phase of the subject is input to the learned model D61. The combination of the dynamic image data related to the early vascular phase, the dynamic image data related to the arterial predominant phase, and the dynamic image data related to the portal predominant phase is used as the second training input data, so the combination Ja of the dynamic image data related to the early vascular phase, the dynamic image data related to the arterial predominant phase, and the dynamic image data related to the portal predominant phase of the subject is input to the learned model D62. As a result, it is possible to learn dynamic moving of bubbles included in the contrast agent.

Further, the contrast image data may be one dynamic image data which is composed of multiple continuous frames and is classified into multiple time phases by an index. In this case, the combination of partial image data of the dynamic image related to the early vascular phase divided by the index and the partial image data of the dynamic image related to the arterial dominant phase divided by the index is used as the first training input data. The combination Ha of the partial image data of the dynamic image related to the early vascular phase of the subject divided by the index, and the partial image data of the dynamic image related to the arterial predominant phase of the subject divided by the index, is input to the learned model D61.

According to the medical image processing apparatus M6, in addition to the effect of the medical image processing apparatus M5, it is possible to acquire a more accurate diagnostic result.

9. Medical Image Processing Apparatus According to the Seventh Embodiment

In the fifth and sixth embodiments described above, the case where the image acquiring function 171 acquires contrast image data live, and where the diagnostic result generating function 174 generates the confirmed diagnostic result data of the subject in substantially real time every time the contrast image data being acquired is described. However, it not limited to this case.

For example, the operator may operate the screen displayed on the display 40 to perform the process of generating the definite diagnostic result data of the subject. This case will be described as a medical image processing apparatus 147 (shown in FIGS. 1 and 10) according to the seventh embodiment.

The configuration and function of the medical image processing apparatus M7 according to the seventh embodiment are the same as those shown in FIGS. 1 and 10. The operation of the medical image processing apparatus 147 according to the seventh embodiment is equivalent to that shown in FIG. 11. Therefore, their description is omitted.

In step ST15 shown in FIG. 11, an operation via the input interface 30 sets a certain time phase in the arterial predominant phase in addition to a certain time phase in the early vascular phase. When a certain time phase in the arterial predominant phase is set in addition to a certain time phase in the early vascular phase, the diagnostic result generating function 174 inputs the combination of the contrast image data in the set time phase to the learned model D5 (shown in FIG. 13) or learned model D61 (shown in FIG. 16A), thereby generates definite diagnostic result data of the subject.

Figure 17A:
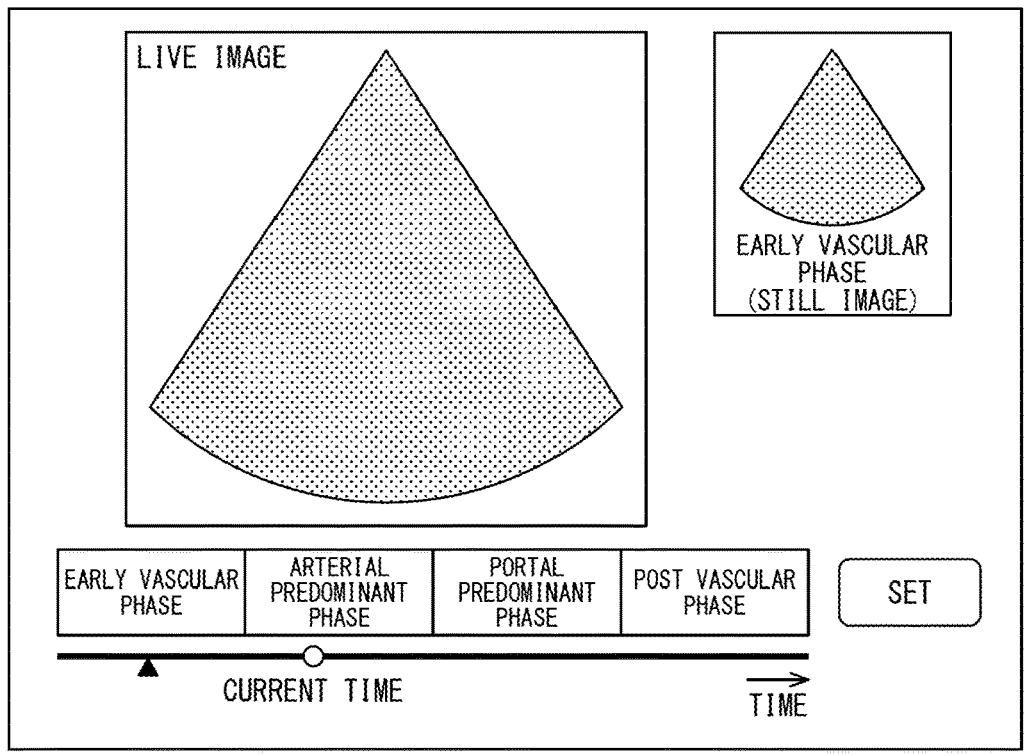
FIG. 17A is a diagram showing an example of a time phase setting screen in the medical image processing apparatus according to the embodiment.
Figure 17B:
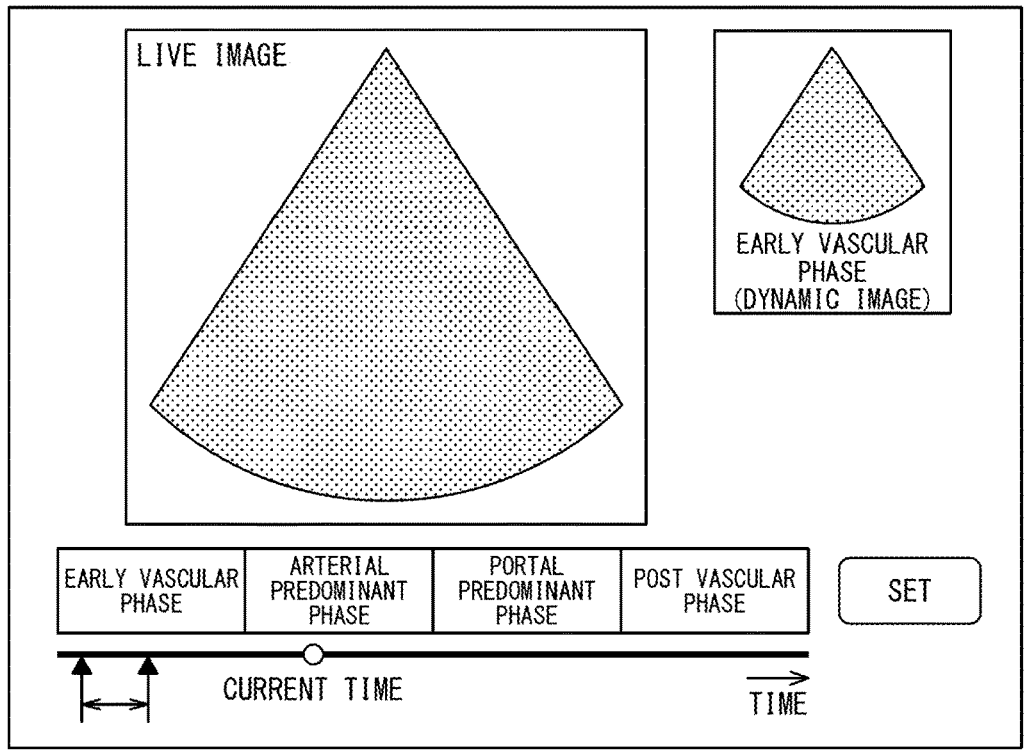
FIG. 17B is a diagram showing an example of a time phase setting screen in the medical image processing apparatus according to the embodiment.

Each of FIGS. 17A and 17B is a diagram showing an example of a time phase setting screen.

The upper part of FIG. 17A shows the contrast image data displayed live. The lower part of FIG. 17A shows time phases each predetermined by the elapsed time with reference to the start of contrast agent injection, the actual elapsed time (time slider) with reference to the start of contrast agent injection, and the "Set" button.

While confirming the time slider, the operator clicks the "set" button via the input interface 30 when the contrast image data effective for diagnosis appears as a live image in each time phase. When the "Set" button is clicked in the early vascular phase, a certain time in the early vascular phase is set. Then, a mark is shown in the corresponding time phase of the time slider such that the set time can be visually recognized, and the contrast image data at the set time is displayed as a still image in the upper right.

When the "set" button is clicked in the arterial predominant phase, a certain time in the arterial predominant phase is set. According to the setting of contrast image data via the input interface 30, the diagnostic result generating function 174 is possible to set time phase data according to the set contrast image data as the time phase data to be input to learned model.

Similar to FIG. 17A, FIG. 17B shows live displayed contrast image data, time phases, a time slider, and a "Set" button.

While confirming the time slider, the operator clicks the "Set" button via the input interface 30 when the contrast image data effective for diagnosis appears as a live image in each time phase. In addition, when the contrast image data effective for diagnosis disappears, the "Set" button is clicked via the input interface 30. When the "Set" button is clicked twice in the early vascular phase, a certain time width in the early vascular phase is set. Then, marks are shown on the corresponding set two time phases of the time slider such that the set time phases can be visually recognized, and multiple contrast image data between the set two time phases are displayed as a dynamic image in the upper right.

When the "Set" button is clicked twice in the arterial predominant phase, a certain time width in the arterial predominant phase is set. According to the setting of the contrast image data via the input interface 30, the diagnostic result generating function 174 is possible to set time phase data corresponding to the set two contrast image data as the time phase data to be input to learned model.

Figure 18:
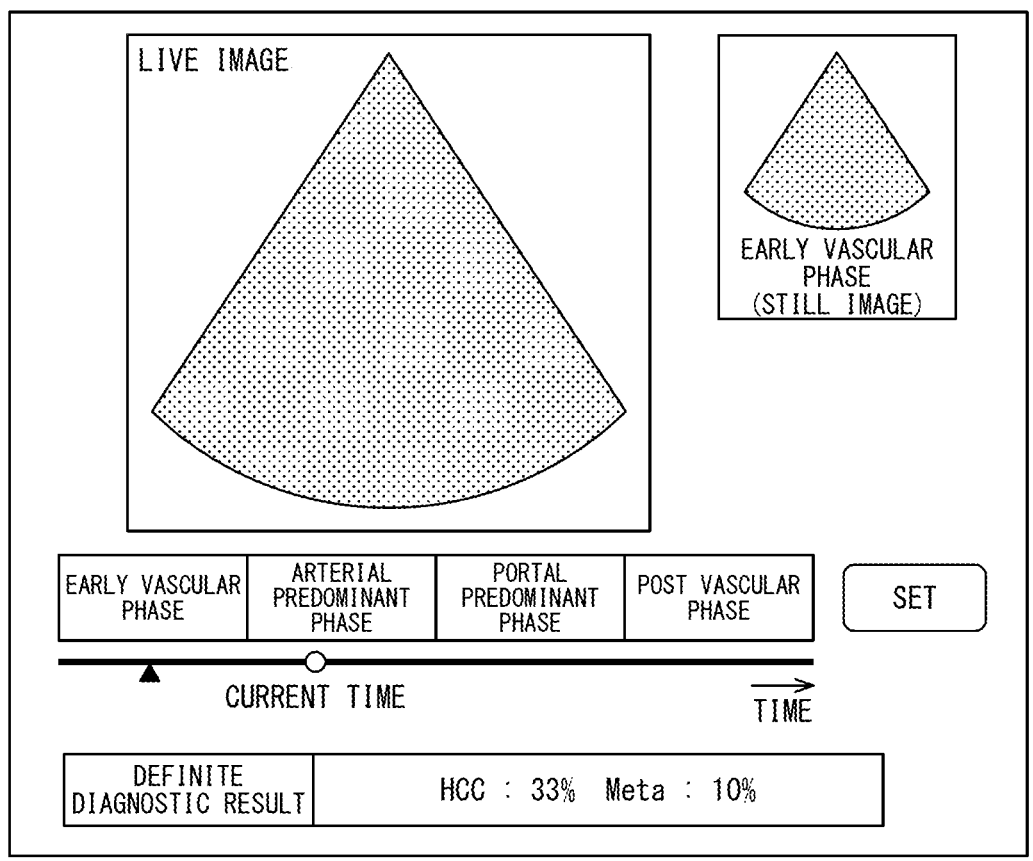
FIG. 18 is a diagram showing a display example of definitive diagnostic result data in the medical image processing apparatus according to the embodiment.

Further, it may be configured such that the definite diagnostic result data generated according to the combination of the set contrast image data is displayed on the setting screen each time. FIG. 18 shows an example in this case.

FIG. 18 is a diagram showing a display example of definitive diagnostic result data.

FIG. 18 shows definite diagnostic result data generated according to a combination of contrast image data related to the time phase set on the time phase setting screen of FIG. 17A. Similar to FIG. 17B, it is possible to display the definitive diagnostic result data.

when a time is set in the arterial predominant phase, the diagnostic result generating function 174 generates definite diagnostic result data "HCC: 30%" and "Meta: 10%" based on the combination. The combination is a combination of the contrast image data of a time set in the early vascular phase and the contrast image data of a time set in the arterial predominant phase. The output control function 175 displays the definite diagnostic result data "HCC: 30%" and "Meta: 10%" on the display 40 as shown in the lower part of FIG. 18.

According to the medical image processing apparatus M7, it is possible to carefully select the data to be input to the learned model. Therefore, in addition to the effect obtained by the medical image processing apparatus M5, it is possible to acquire the diagnostic result at a higher speed and save the hardware resource.

10. Medical Image Processing Apparatus According to the Eighth Embodiment

In the above fifth to seventh embodiments, the case where the image acquiring function 171 acquires the contrast image data live and the diagnostic result generating function 174 generates the definite diagnostic result data of the subject in substantially real time has been described. That is the case where the time phase data of each contrast image data is known. Here, the case where the time phase data of each contrast image data is unknown will be described as the medical image processing apparatus M8 (shown in FIGS. 1 and 10) according to the eighth embodiment. When the time phase data of each contrast image data is unknown, the case where the image acquiring function 171 acquires multiple contrast image data from the image memory 15 after imaging, and where the diagnostic result generating function 174 generates post process definite diagnostic result data based on multiple contrast image data is included. The case where the diagnostic result generating function 174 generates the confirmed diagnostic result data in substantially real time is included.

The diagnostic result generating function 174 generates time phase data by inputting contrast image data to the learned model. The learned model is for generating the time phase data based on the contrast image data acquired by the image acquiring function 171. The time phase data is classified according to a contrast state of the lesion area with the contrast agent included in the contrast image data.

The method of generating the time phase data in the medical image processing apparatus M7 is the same as that described with reference to FIGS. 9A and 9B. Therefore, the description is omitted. In the method of generating time phase data in the medical image processing apparatus M7, the "needfulness data generating function 172" shown in FIGS. 9A and 9B is simply replaced with the "diagnostic result generating function 174".

According to the medical image processing apparatus M8, it is possible to estimate not only the elapsed time based on the start of contrast agent injection but also the time phase data based on the contrast image data. Further, by applying the estimated time phase data to the fifth to seventh embodiments, it is possible to perform a definite diagnosis of the tumor without depending on the experience or subjectivity of an operator such as a doctor in the post process after imaging.

11. First Modification

In the above fifth to eighth embodiments, the case where the training input data or the input to the learned model is a combination of n contrast image data generated in each of n time phases, and the case where the combination of n contrast image data generated in each of the n time phases and the supplementary information such as identification information have been described. However, it is not limited to those cases. At least one of the B-mode image data, the color Doppler image data, and the power Doppler image data may be added to the training input data or the input to the learned model.

The image data to be added may be image data related to the corresponding one time phase, or may be two image data generated in the corresponding two time phases. The B-mode image data includes so-called B-mode image data generated by imaging that is different from the contrast image data generated by CHI, and fundamental image data and the like generated from the reflected wave data (received signal) of the fundamental wave component. The fundamental image data is generated in the same scan as the contrast image.

According to the first modification of the medical image processing apparatuses M5 to M8, it is possible to acquire more accurate diagnostic results in addition to the effects of the medical image processing apparatuses M5 to M8.

12. Second Modification

In the medical image processing devices M5 to M8 according to the above fifth to eighth embodiments, the case where the training input data and the input to the learned model are two contrast image data generated in respective two time phases, and the case where the combination of two contrast image data generated in two respective time phases and supplementary information such as identification information have been described. However, it is not limited to those cases. BTI (Bubble Tracking Imaging) image data, which is image data representing a tracking locus of bubbles, may be added to the training input data and the input to the learned model.

The added BTI image data is image data showing the trajectory of the bubbles up to the frame concerned, which relates to the corresponding one temporal phase.

The case where BTI image data is added to the combination of the two contrast image data generated in each of the two time phases as the input to the training input data and the learned model has been described. However, it is not limited to this case. As the input to the training input data or the learned model, BTI image data may be adopted instead of the combination of the two contrast image data generated in each of the two time phases.

According to the second modification of the medical image processing apparatuses M5 to M8 according to the fifth to eighth embodiments, in addition to the effects of the medical image processing apparatuses 145 to 148, it is possible to acquire more accurate diagnostic result.

13. Third Modification

In the fifth to eighth embodiments described above, the definite diagnostic result data is generated every time a combination occurs live, but the present invention is not limited to this case.

It should be noted that the case where the image acquiring function 171 acquires contrast image data live and the diagnostic result generating function 174 generates definite diagnostic result data in substantially real time has been described with reference to FIGS. 17 and 18. However, it is not limited to this case. The image acquiring function 171 may acquire multiple contrast image data from the image memory 15 after the imaging is completed. The diagnostic result generating function 174 may generate post-determined diagnostic result data based on a combination of multiple contrast image data.

For example, the diagnostic result data of the subject regarding the tumor may be generated based on the needfulness data generated by the medical image processing apparatuses M1 to M4 according to the above-described first to fourth embodiments.

14. Medical Image Processing Apparatus According to the Ninth Embodiment

Figure 19:
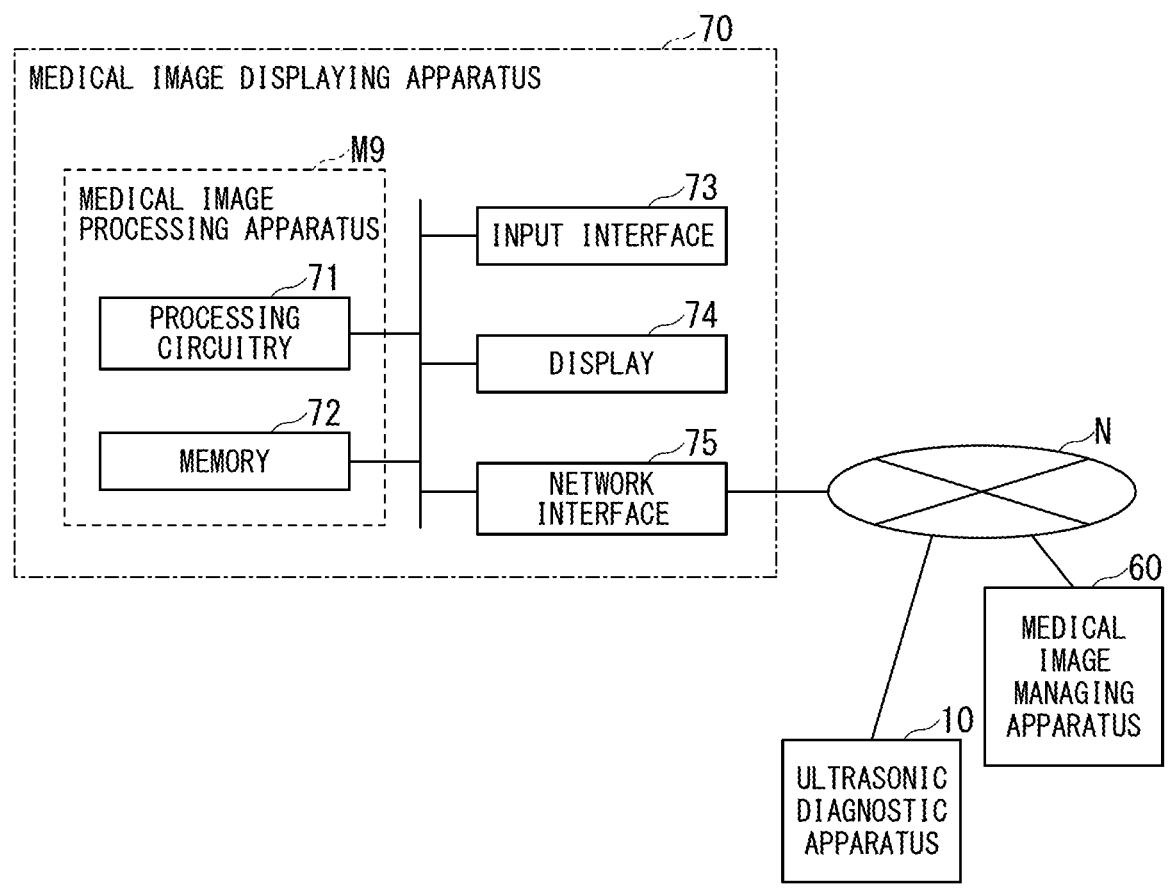
FIG. 19 is a schematic diagram showing a configuration of a medical image displaying apparatus including the medical image processing apparatus according to the embodiment.

FIG. 19 is a schematic diagram showing a configuration of a medical image displaying apparatus including the medical image processing apparatus according to the ninth embodiment. FIG. 19 shows a medical image displaying apparatus 70 including a medical image processing apparatus M9 according to the ninth embodiment. The medical image displaying apparatus 70 is a medical image management apparatus (image server), a workstation, an image interpretation terminal, or the like, and is provided on the medical image system connected via a network. The medical image displaying apparatus 70 may be an offline device.

The medical image displaying apparatus 70 includes processing circuitry 71, a memory 72, an input interface 73, a display 74, and a network interface 75. The processing circuitry 71 and the memory 72 form a medical image processing apparatus 519. Alternatively, the medical image processing apparatus M9 may be configured by adding at least one of the input interface 73 and the display 74 to the processing circuitry 71 and the memory 72.

The processing circuitry 71, the memory 72, the input interface 73, and the display 74 have the same configuration as the processing circuitry 17, the main memory 18, the input interface 30, and the display 40 shown in FIGS. 1 and 10. Therefore, their description is omitted.

The network interface 75 is composed of a connector according to a parallel connection specification or a serial connection specification. When the medical image displaying apparatus 70 is provided on the medical image system, the network interface 75 transmits/receives information to/from an external apparatus on the network. For example, the network interface receives medical image data such as contrast image data from an external apparatus under the control of the processing circuitry 71.

Subsequently, the function of the medical image displaying apparatus 70 including the medical image processing apparatus M9 will be described.

Figure 20:
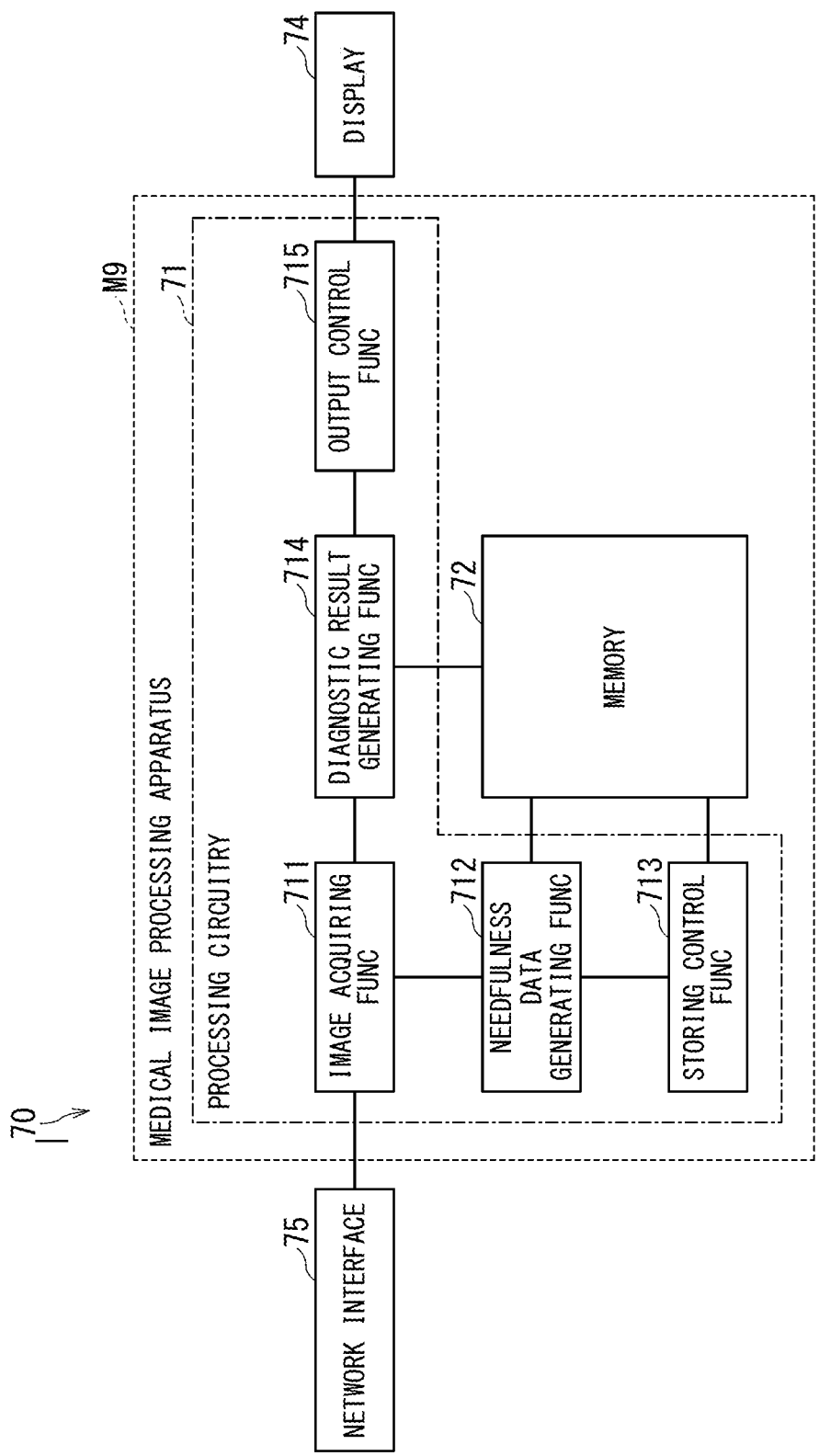
FIG. 20 is a block diagram showing functions of the medical image displaying apparatus including the medical image processing apparatus according to the embodiment.

FIG. 20 is a block diagram showing functions of the medical image displaying apparatus 70 including the medical image processing apparatus M9.

The processing circuitry 71 executes a program stored in the memory 72, thereby realizes a processed image acquiring function 711, a needfulness data generating function 712, a storing control function 713, a diagnostic result generating function 714, and an output control function 715. Note that all or some of the functions 711 to 715 are not limited to being realized by executing the program of the medical image processing apparatus M9. The medical image displaying apparatus 70 may be provided as a circuit such as the ASIC.

The image acquiring function 711 includes a function of acquiring contrast image data from the medical image management apparatus 60 or the ultrasonic diagnostic apparatus 10 via the network interface 75. The image acquiring function 711 is one example of an image acquiring unit.

The needfulness data generating function 712 includes a function equivalent to the needfulness data generating function 172 shown in FIG. 2. The needfulness data generating function 712 is one example of a processing unit.

The storing control function 713 includes a function equivalent to the storing control function 173 shown in FIG. 2. The storing control function 713 is one example of a storing control unit.

The diagnostic result generating function 714 includes a function equivalent to the diagnostic result generating function 174 shown in FIG. 10. The diagnostic result generating function 714 is one example of a processing unit.

The output control function 715 includes a function equivalent to the output control function 175 shown in FIG. 10. The output control function 715 is one example of the output control unit.

When remotely controlling the ultrasonic diagnostic apparatus 10 via the network N, the medical image processing apparatus M9 acquires a live image from the ultrasonic diagnostic apparatus 10, thereby generates the needfulness data and the definitive diagnostic result data, using the contrast image data as the live image. Further, the medical image processing apparatus M9 acquires the contrast image data after completion of imaging from the ultrasonic diagnostic apparatus 10 or the medical image management apparatus 60 via the network N, thereby generates the needfulness data and the definitive diagnostic result data by post processing. The operation of the medical image displaying apparatus 70 is the same as the operation of the ultrasonic diagnostic apparatus 10 shown in FIG. 3 or 11. Therefore, the description is omitted.

According to the medical image processing apparatus M9, it is possible to perform a definite diagnosis of the tumor by using an apparatus different from the medical image generating apparatus without depending on the experience or subjectivity of an operator such as a doctor. Further, according to the medical image processing apparatus M9, it is possible to support definitive diagnosis of the tumor based on multiple contrast image data acquired in multiple different time phases, so as to possibly make a definite diagnosis of the tumor without depending on the experience or subjectivity of an operator such as a doctor.

According to at least one embodiment described above, it is possible to make a definite diagnosis of the tumor without depending on the experience or subjectivity of an operator such as a doctor.

Each of the image acquiring functions 171 and 711 is one example of an image acquiring unit. Each of the needfulness data generating functions 172 and 712 is one example of a processing unit. Each of the storing control functions 173 and 713 is one example of a storing control unit. Each of the diagnostic result generating functions 174 and 714 is one example of a processing unit. Each of the output control functions 175 and 715 is one example of an output control unit.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
acquire contrast image data generated by imaging a subject,
input the acquired contrast image data to a first learned model to generate a needfulness data regarding storage of the acquired contrast image data, the first learned model being for generating the needfulness data based on the acquired contrast image data, and
input contrast image data determined to need to be stored based on the generated needfulness data to a second learned model to generate a time phase data classified according to a contrast state of a lesion area with a contrast agent included in the acquired contrast image data, the second learned model being for generating the time phase data based on the contrast image data.

2. The medical image processing apparatus according to claim 1, wherein
the first learned model is one learned model based on multiple contrast image data related to multiple time phase data, and
the processing circuitry is configured to input the acquired contrast image data to the one learned model to acquire the needfulness data.

3. The medical image processing apparatus according to claim 1, wherein
the first learned model includes multiple learned models each corresponding to a combination of multiple contrast image data related to multiple time phase data, and
the processing circuitry is configured to input a combination of acquired multiple contrast image data to a learned model corresponding to the time phase of the multiple learned models to acquire the needfulness data.

4. The medical image processing apparatus according to claim 1, wherein the processing circuit is configured to store the acquired contrast image data in a memory according to the needfulness data.

5. The medical image processing apparatus according to claim 1, wherein
the first learned model is further generated based on at least one additional image data of B-mode image data, color Doppler image data, and power Doppler image data, and
the processing circuitry is further configured to input the additional image data of the subject to the first learned model to generate the needfulness data.

6. The medical image processing apparatus according to claim 1, wherein the acquired contrast image data is frame image data or dynamic image data.

7. The medical image processing apparatus according to claim 1, wherein the processing circuitry is configured to acquire contrast image data generated by ultrasonic imaging of a liver as the imaging of the subject.

8. A medical image processing apparatus comprising:
processing circuitry configured to
acquire contrast image data generated by imaging a subject,
generate a first learned model based on the acquired contrast image data and a needfulness data regarding storage of the acquired contrast image data, and
generate a second learned model based on the acquired contrast image data and a time phase data classified according to a contrast state of a lesion area with a contrast agent included in the acquired contrast image data.

* * * * *